(12) United States Patent
Mironov

(10) Patent No.: US 7,919,678 B2
(45) Date of Patent: Apr. 5, 2011

(54) METHOD FOR MODIFYING PLANT GROWTH CHARACTERISTICS

(75) Inventor: Vladimir Mironov, Ghent (BE)

(73) Assignee: Cropdesign N.V., Zwijnaarde (BE)

( * ) Notice: Subject to any disclaimer, the term of this patent is extended or adjusted under 35 U.S.C. 154(b) by 0 days.

(21) Appl. No.: 10/544,501

(22) PCT Filed: Feb. 6, 2004

(86) PCT No.: PCT/EP2004/050092
§ 371 (c)(1),
(2), (4) Date: Aug. 4, 2005

(87) PCT Pub. No.: WO2004/070027
PCT Pub. Date: Aug. 19, 2004

(65) Prior Publication Data
US 2006/0037106 A1    Feb. 16, 2006

(30) Foreign Application Priority Data
Feb. 6, 2003    (EP) ................................ 03075363

(51) Int. Cl.
*C12N 15/82* (2006.01)
*C12N 15/87* (2006.01)
*C07H 21/04* (2006.01)
(52) U.S. Cl. ....... 800/278; 800/284; 536/23.2; 536/23.6
(58) Field of Classification Search ........................ None
See application file for complete search history.

(56) References Cited

U.S. PATENT DOCUMENTS
5,885,820 A     3/1999 Chang
2003/0200559 A1* 10/2003 Butler et al. ................. 800/278

FOREIGN PATENT DOCUMENTS
EP     1 033 405     9/2000

OTHER PUBLICATIONS

Datta, et. al., Protection of translation initiation factor eIF2 phosphorylation correlates with eIF2-associated glycoprotein p67 levels and requires the lysine-rich domain I of p67. Biochimie—919-931 (2001).*
Giglione (2000) Identification of eukaryotic peptide deformylases reveals universality of N-terminal protein processing mechanisms EMBO Journal 19, 5916-5929.*
Broun, et al., (1998) Catalytic Plasticity of Fatty Acid Modification Enzymes Underlying Chemical Diversity of Plant Lipids. Science 282(13) 1315-1317.*
Lazar et al., (1988) Transforming Growth Factor A: Mutation of Aspartic Acid 47 and Leucine 48 in Different Biological Activities. Molec. & Cell. Biol. 8(3)1247-52.*
Guo et al., (2004) Protein Tolerance to Random Amino Acid Change P.N.A.S. 101 (25) 9205-9210.*
De Pater et al (1992) Plant J. 2(6) 837-844).*
De Pater et al (1992) The promoter of the rice gene GOS2 is active in various different monocot tissues and binds rice nuclear factor ASF-1. Plant J. 2(6) 837-844.*
http://ca.expasy.org/cgi-bin/get-prodoc-entry?PDOC00575.*
Bazan,J.F., Sequence and structure comparison suggest that methionine aminopeptidase, prolidase, aminopeptidase P, and creatinase share a common fold. Proc Natl Acad Sci U S A (1994) 91, 2473-2477.*
http://pfam.janelia.org/family?acc=PF00557.*
International Search Report for PCT/EP2004/050092 dated Sep. 2, 2004.
Giglione et al., *Identification of Eukaryotic Peptide Deformylases Reveals Universality of N-Terminal Protein Processing Mechanisms*, EMBO Journal, vol. 19, No. 21, Nov. 1, 2000, pp. 5916-5929, XP000999120.
Giglione, et al., *Arabidopsis thaliana putative methionine aminopeptidase mRNA*, Database EBI, Nov. 28, 2000, XP002293725, database accession No. AF300880.
Alexandrov, et al., *New sequence determined DNA fragments (SDFs) from different plant species*; Seq. ID No. 13474 of EP1033405, Database EBI, Oct. 17, 2000, XP002293726, database accession No. AAC36349.
Alexandrov, *New sequence determined DNA fragments (SDFs) from different plant species*; Seq. ID No. 50197 of EP1033405, Database EBI, Sep. 6, 2000, XP002293727, database accession No. AAC46453.
Bradshaw, et al., *N-Terminal processing: the methionine aminopeptidase and N<a>lpha-acetyl transferase families*, Tibs Trends in Biochemical Sciences, vol. 23, No. 7, Jul. 1, 1998, pp. 263-267, XP004126979.

* cited by examiner

*Primary Examiner* — Li Zheng
(74) *Attorney, Agent, or Firm* — Nixon & Vanderhye P.C.

(57) ABSTRACT

The present invention concerns a method for modifying plant growth characteristics by modifying expression in a plant of a nucleic acid encoding a methionine aminopeptidase (MAP protein) and/or by modifying level and/or activity in a plant of a MAP protein. The invention also relates to transgenic plants having modified growth characteristics, which plants have modified expression of a nucleic acid encoding a MAP protein. Particularly the present invention discloses a method to increase yield of a plant, preferably in a cereal such as rice or corn.

11 Claims, 7 Drawing Sheets

Figure 1:
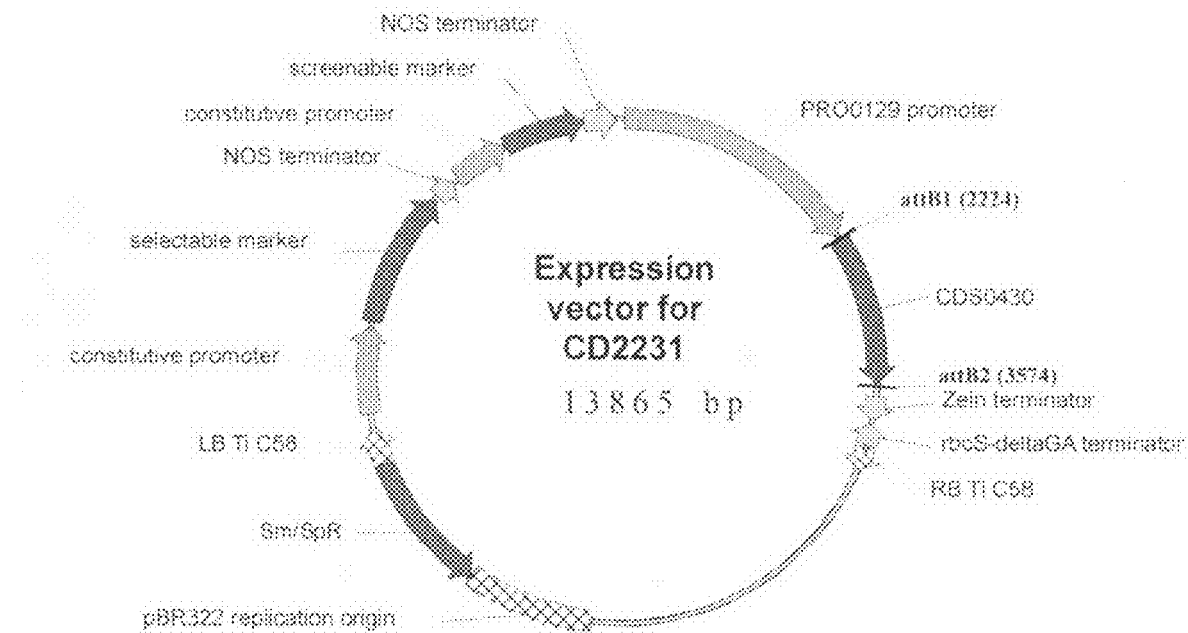

**SEQ ID NO 1: CDS0430 *Arabidopsis thaliana* cDNA MAP2B** atggcgagcgaaagtcctgatgttgctgttgtagctccggtggtggagaatggcggcgctg
agtcctctaatggtaaagaggaacaattggaatctgagctttcgaagaagcttgagattgc
agaagatggtcaagaggagaacgatggagaagaaggaagcaaagctgagacttcaacgaag
aagaagaagaagaaaaataaaagcaagaagaagaaggaactccctcaacagactgatccac
cttcaattcctgtcgttgagctcttcccatcaggagagtttcctgaaggtgaaatccaaga
gtataaggatgataatctttggagaacaacatctgaagagaagagagagctggagcgtttt
gaaaagccaatatataactctgttcgccgagctgcagaagttcatcgccaggttcgtaaat
atgtcagaagcatagtgaagcctggaatgttgatgactgatatatgtgagaccctagagaa
tactgttcgtaagttgatatcagagaatggtcttcaagctggtattgcattccctacagga
tgctctttgaattgggtcgctgctcattggacaccaaactctggagataagactgtacttc
agtacgacgatgttatgaaattggactttggaacacatattgatgggcatattattgactg
tgcatttacagttgccttcaacccatgttcgatcctctcttagcagcctctcgtgaagct
acgtataccggtatcaaggaagctgggatcgatgtccgtctctgtgatatcggtgctgcta
ttcaggaggtcatggagtcttatgaggttgaaatcaacggaaaggtcttccaagttaaaag
tatccgaaacttgaatggtcacagcattggaccctatcagatacatgctgggaaatctgtt
cctatcgtaaaaggaggcgagcagacaaagatggaagagggcgagttttatgccatcgaaa
catttggatcaaccgggaaaggatatgtgagagaagacctagaatgtagccattacatgaa
gaactttgacgctggccacgtccccttgaggttgcctagagcaaaacaactccttgcaacc
attaacaagaatttctcgactctcgccttctgcagacgttatttggaccgcattggtgaaa
ccaaatacttaatggctctaaagaatctttgtgactctggcattgttcagccgtatcctcc
tctgtgtgatgtgaaaggaagctatgtatcacagtttgaacacaccattttactgcgacct
acttgcaaagaagttctctccaagggagacgactactga

**SEQ ID NO 2: *Arabidopsis thaliana* protein MAP2B**

MASESPDVAVVAPVVENGGAESSNGKEEQLESELSKKLEIAEDGQEENDGEEGSKAETSTK
KKKKKNKSKKKKELPQQTDPPSIPVVELFPSGEFPEGEIQEYKDDNLWRTTSEEKRELERF
EKPIYNSVRRAAEVHRQVRKYVRSIVKPGMLMTDICETLENTVRKLISENGLQAGIAFPTG
CSLNWVAAHWTPNSGDKTVLQYDDVMKLDFGTHIDGHIIDCAFTVAFNPMFDPLLAASREA
TYTGIKEAGIDVRLCDIGAAIQEVMESYEVEINGKVFQVKSIRNLNGHSIGPYQIHAGKSV
PIVKGGEQTKMEEGEFYAIETFGSTGKGYVREDLECSHYMKNFDAGHVPLRLPRAKQLLAT
INKNFSTLAFCRRYLDRIGETKYLMALKNLCDSGIVQPYPPLCDVKGSYVSQFEHTILLRP
TCKEVLSKGDDY

FIGURE 2A

**SEQ ID NO 3: *Arabidopsis thaliana* cDNA MAP1A**

```
ggcgattttgagattgttctctgattggcttaatccgagagaatcaaggaattgaatggcc
agtgaatcagatgcatcgagcattgctactcttcctgtgctcgctgcgagaagcctgcac
atcttcagtgtccgaaatgcatagacttaaagcttcctcgtgaacaagcctctttctgcac
tcaagaatgtttcaaggcagcttggagctcgcacaaatcagtacatgtgaaagctcagctg
tcttcaatcggtgatcagaactctgatcttatttctcaaggctggctctattgcgtcaaga
aaggccaggctagaacacctaagcttccacactttgattggactgggcctctaaagcaata
tcccatatctaccaagcgtgttgtgcctgctgagattgagaaacctgactgggcaattgat
gggactcccaaagttgaaccgaatagtgatctacaacatgttgttgagataaaaacgcctg
aacaaatccagagaatgcgtgaaacctgtaaaattgccagagaggtcctggatgcagccgc
tagggtgattcaccccggtgtgactactgatgagattgatcgagtagttcatgaagcaact
attgcagcaggaggatatccatcgcccctcaactactatttctttccgaaatcttgctgca
catctgttaatgaagtaatttgtcatggaattccggatgctaggaaactagaagatggtga
tatagtaaatgtggatgtaacagtctgttataaaggttgccatggtgaccttaatgagaca
tactttgttggaaacgttgacgaagcatcacgtcaactggttaagtgcacatacgagtgcc
tggagaaagctatagcaattgttaaacctggagtaagatttcgtgaaattggagagatagt
caaccgccatgctacaatgtctgggttatcagtggtgagatcttattgtggtcatggtatt
ggagatcttccattgtgctccaaacattcctcactatgcaagaaacaaagcagttggag
tgatgaaagcaggtcagactttcacaatcgagccaatgatcaacgcaggggggtggaggga
tcgaacatggcctgatggatggactgcagttaccgcagatggaaaacgcagcgctcagttt
gagcatacctattggtaacggagactggtgttgaggttttaacagcgaggcttccttcat
cgcctgacgtatatccttggcttaccaagtgattaagtgtttggttccttttttggttgtga
ttcgtaaacttgggaataatagtgtcatcttttgccattatagaccatttgatgttgtta
ccttgttgtctttgtttatgtaatttattattactatctgaaactgaatcttaaagacag
agtcatactgtttcaa
```

**SEQ ID NO 4: *Arabidopsis thaliana* protein MAP1A**

```
MASESDASSIATLSCARCEKPAHLQCPKCIDLKLPREQASFCTQECFKAAWSSHKSVHVKA
QLSSIGDQNSDLISQGWLYCVKKGQARTPKLPHFDWTGPLKQYPISTKRVVPAEIEKPDWA
IDGTPKVEPNSDLQHVVEIKTPEQIQRMRETCKIAREVLDAAARVIHPGVTTDEIDRVVHE
ATIAAGGYPSPLNYYFFPKSCCTSVNEVICHGIPDARKLEDGDIVNVDVTVCYKGCHGDLN
ETYFVGNVDEASRQLVKCTYECLEKAIAIVKPGVRFREIGEIVNRHATMSGLSVVRSYCGH
GIGDLFHCAPNIPHYARNKAVGVMKAGQTFTIEPMINAGGWRDRTWPDGWTAVTADGKRSA
QFEHTLLVTETGVEVLTARLPSSPDVYPWLTK
```

SEQ ID NO 5: MAP1 signature consensus sequence

[MFY]-x-G-H-G-[LIVMC]-[GSH]-x(3)-H-x(4)-[LIVM]-x-[HN]-[YWVH]

FIGURE 2B

SEQ ID NO 6: MAP2 signature consensus sequence

[DA]-[LIVMY]-x-K-[LIVM]-D-x-G-x-[HQ]-[LIVM]-[DNS]-G-x(3)-[DN]

SEQ ID NO 7: peptidase_M24 domain of AtMAP1A

RSYCGHGIGDLFHCAPNIPHYARNKAVGVMKAGQTFTIEPMINAGGWRDRTWPDGWTAVTA
DGKRSAQFEHTLL

SEQ ID NO 8: peptidase_M24 domain of AtMAP2B

RNLNGHSIGPYQIHAGKSVPIVKGGEQTKMEEGEFYAIETFGSTGKGYVREDLECSHYMKN
FDAGHVPLRLP

SEQ ID NO 9: lysine-rich domain of AtMAP2B

KKKKKKNKSKKKK

SEQ ID NO 10: Primer prm01642

ACAAGTTTGTACAAAAAAGCAGGCTTCACAATGGCGAGCGAAAGTCC

SEQ ID NO 11: Primer prm01643

ACCCAGCTTTCTTGTACAAAGTGGTAGGATCTGAATCAGTAGTCGTCTC

FIGURE 2C

```
Arath_MAP2A_CDS0431   ----MAIGNPEVATME--KENTEAES------SNGNESQLSSDLTKSLD---------  37
AtMAP2B_CDS0430       ----MASESPDVAVVAPVVENGGAES------SNGKEEQLESELSKKLE---------  39
oryza_BAD03108        ----MVRGSVDVAIKEMEALCIGQNQETKEEVGFETQEASLKASKVADSK--------  46
Orysa_AK122063        ----MAGGSADAVTKEMEALLVGQNP---NAVSGETCETSSKEGKVADSN--------  43
Zeama_AY105027        ------MAAVDATTKEMDALHVGQND--------ETKETLIKEDKAANSNHS------  38
RatMetAP2             ------MAGVEEASSFGGHLNRDLDPDDREEGTSSTAEEAAKKKRRKKKKGKGAVSAGQQ  54
MouseMetAP2           ------MAGVEQAASFGGHLNGDLDPDDREEGTSSTAEEAAKKKRRKKKKGKGAVSAVQQ  54
humanMetAP2           ------MAGVEEVAASGSHLNGDLDPDDREEGAASTAEEAAKKKRRKKKKSKGPSAAGEQ  54
drosophilaMetAP2      ------MSATETLN------------VEAATPEIGEEVKKQKKPKPNNKK-------  32
YeastMetAP2           ------MTDAEIENSPAS---------------DLKELNLENEGVEQQD---------  28
Orysa_AK107616        ------MTAVPPENGMANLDI------------SGKDAPAKTNGANGNN---------  31
Arath_MAP1A           MASESDASSIATLSCARCEKPAHLQCPKCIDLKLPREQASFCTQECFKAAWS-------  52
human_MAP1            ---------------------------------------------------------
yeast_MAP1            -------MSTATTTVTTSDQASHPTKIYCSGLQCGRETSS-------QMKCP-------  38
Arath_MAP1B           ------MASSVFLSSFSSSSSLQLCSSFHGEYLAPSRCFIGAPVTSSSLSLS-------  46
Arath_MAP1C           ----------MLQKIS--QSISLCN---GDQFKPLIYLAGAPTNFISSPLS-------  36
Arath_MAP1D           ------MAGVKSLQPRLISSFLGNNS---IRSTQPLIHLFRFDLGRRHVSMQ-------  43

K-rich
Arath_MAP2A_CDS0431   --------------LAEVKEDEKDNNQEEDGLKAEAST------------KKKKKKSKS  70
AtMAP2B_CDS0430       --------------IAEDGQEENDG---EEGSKAETST------------KKKKKKNKS  69
oryza_BAD03108        -----------GAPYSPPEN-DDD-AEVDYPSQDGAQVKIISLQGTVIAAKKKKKKSKA  92
Orysa_AK122063        -------------GSHSSPPED-DDDEAQGDGPSQDGGSE----------AAKKKKKSKS  80
Zeama_AY105027        ---------VVAAQSLPPEDDDDDEAQADGPSQDGAAA---------AVKKKKKKNKS  78
RatMetAP2             ELDKESGTSVDEVAKQLERQALEEKEKDDDDEDGDGDGD----------GAAGKKKKKK  103
MouseMetAP2           ELDKESGALVDEVAKQLESQALEEKERDDDDEDGDGDAD----------GATGKKKKKK  103
humanMetAP2           EPDKESGASVDEVARQLERSALEDKERDEDDEDGDGDGD----------GATGKKKKKK  103
drosophilaMetAP2      --------LRQEAARKIASGEGGDEELTTNGDAKPATPA----------AQPAKKKGNK  73
YeastMetAP2           ---------------QAKADESDPVES---------------------KKKKNKKKK  49
Orysa_AK107616        ---------------DVENDNSDDDEAEEGGEGAGEGAA----------KKKKRKRPRK  65
Arath_MAP1A           ----------------SHKSVHVKAQLSSIGDQNSDLISQGWLYCVKKGQARTPK-LPH  94
human_MAP1            ---------------------------------------------------------
yeast_MAP1            ----------------VCLKQGIVSIFCDTSCYENNYKAHKALHNAKDGLEGAYDPFPK  81
Arath_MAP1B           ----------------GKKNSYSPRQFHVSAKKVSGLEEAIRIRKMRELETKSKVRRNP  89
Arath_MAP1C           ----------------GKKKSSS--------------LRIKRIQQLQSTLEDRINP  62
Arath_MAP1D           ----------------LSRTFSG---------------LTDLLFNRRNEDEVIDGKRK  70

Arath_MAP2A_CDS0431   KKKKSS--LQQTDPPSIPVLELFPSGDFPQGEIQQYNDDN--------LWRTTSEEKREM  120
AtMAP2B_CDS0430       KKKKEL--PQQTDPPSIPVVELFPSGEFPEGEIQEYKDDN--------LWRTTSEEKREL  119
oryza_BAD03108        KKKKGP--LQQTDPPSIPVDELFPSGEFPEGEIQHYKDDN--------LWRTTSEEKREL  142
Orysa_AK122063        KKKKGP--LQQTDPPSIPIDELFPSGDFPEGEIQQYKDDN--------LWRTTSEEKREL  130
Zeama_AY105027        KKKKGP--LQQTDPPSIPVDELFPSGEFPEGEIQQYKDDN--------LWRTTSEEKRDL  128
RatMetAP2             KKKRGP--RVQTDPPSVPICDLYPNGVFPKGQECEYPPTQ---DGRTAAWRTTSEEKKAL  158
MouseMetAP2           KKKRGP--KVQTDPPSVPICDLYPNGVFPKGQECEYPPTQ---DGRTAAWRTTSEEKKAL  158
humanMetAP2           KKKRGP--KVQTDPPSVPICDLYPNGVFPKGQECEYPPTQ---DGRTAAWRTTSEEKKAL  158
drosophilaMetAP2      GKKSG-----QTDPPTIPIAKLYPDGNFPEGEIVEHPTPKDMPDDRTAKDRFTSEEKRAL  128
YeastMetAP2           KKKSN---------VKKIELLFPDGKYPEGAWMDYHQDF-------NLQRTTDEESRYL  92
Orysa_AK107616        KKKAGGGAAAQSSPPRTEVSKLFPNGSYPIGEEVDYLND--------NSYRTTNEEKRAM  117
Arath_MAP1A           FDWTGPLKQ-YPISTKRVVPAEIEKPDWAIDG-TPKVEPN---------SDLQHVVEIK  142
human_MAP1            --------------------MSESEQALKG-TSQIK------------------LL  17
yeast_MAP1            FKYSGKVKASYPLTPRRYVPEDIPKPDWAANG-LPVSEQR---------NDRLNNIPIY  130
Arath_MAP1B           PLRRG------RVSPRLLVPDHIPRPPYVESGVLPDIS-----------SEFQIP  127
Arath_MAP1C           PLVCG------TVSPRLSVPDHILKPLYVESSKVPEIS-----------SELQIP  100
Arath_MAP1D           RLRPG------NVSPRRPVPGHITKPPYVDSLQAPGIS-----------SGLEVH  108
```

FIGURE 3A

```
Arath_MAP2A_CDS0431   ERL--QKPIYNSLRQAAEVHRQVRKYMRSILKPGMLMIDLCETLENTVRKLISENGLQA- 177
AtMAP2B_CDS0430       ERP--EKPIYNSVRRAAEVHRQVRKYVRSIVKPGMLMTDICETLENTVRKLISENGLQA- 176
oryza_BAD03108        ERL--QKPMYNAVRRAAEVHRQVRKYMRSILKPGMLMIDLCETLENMVRKLIKENGLEA- 199
Orysa_AK122063        ERL--QKPIYNAVRRAAEVHRQVRKHMRSILKPGMLMIDLCETLENMVRKLIKENGLQA- 187
Zeama_AY105027        ERL--QKPIYNSVRQAAEVHRQVRKYMRSIIKPGMLMVDLCETLENMVRKLIKENGLQA- 185
RatMetAP2             DQA--SEEIWNDFREAAEAHRQVRKYVMSWIKPGMTMIEICEKLEDCSRKLIKENGLNA- 215
MouseMetAP2           DQA--SEEIWNDFREAAEAHRQVRKYVMSWIKPGMTMIEICEKLEDCSRKLIKENGLNA- 215
humanMetAP2           DQA--SEEIWNDFREAAEAHRQVRKYVMSWIKPGMTMIEICEKLEDCSRKLIKENGLNA- 215
drosophilaMetAP2      DRI--NTDIYQELRQAAEAHRQTRQYMQRYIKPGMTMIQICEELENTARRLIGENGLEA- 185
YeastMetAP2           KRDLERAEHWNDVRKGAEIHRRVRRAIKDRIVPGMKLMDIADMIENTTRKYTGAENLLAM 152
Orysa_AK107616        DRD--NMEFLTEYRQAAEVHREVRKYAQQNIKPGMSLTEIAEMIENGTRALTGHQGLEEG 175
Arath_MAP1A           TPE-----QIQRMRETCKIAREVLDAAARVIHPGVTTDEIDRVVHEATIAAGGYPSPLN- 196
human_MAP1            SSE-----DIEGMRLVCRLAREVLDVAAGMIKPGVTTEEIDHAVHLACIARNCYPSPLN-  71
yeast_MAP1            KKD-----QIKKIRKACMLGREVLDIAAAHVRPGITTDELDEIVHNETIKRGAYPSPLN- 184
Arath_MAP1B           GPE-----GIAKMRAACELAARVLNYAGTLVKPSVTTNEIDKAVHDMIIBAGAYPSPLG- 181
Arath_MAP1C           DSI-----GIVKMKKACELAARVLDYAGTLVRPFVTTDEIDKAVHQMVIEFGAYPSPLG- 154
Arath_MAP1D           DKK-----GIECMRASGILAARVRDYAGTLVKPGVTTDEIDEAVHNMIIENGAYPSPLG- 162

MAP2 signature
Arath_MAP2A_CDS0431   ------GIAFPTGCSLNNVAAHWTPNSGDKTVLQYDDVMKLDFGTHIDGHIVDSAFTVAF 231
AtMAP2B_CDS0430       ------GIAFPTGCSLNWVAAHWTPNSGDKTVLQYDDVMKLDFGTHIDGHIIDCAFTVAF 230
oryza_BAD03108        ------GIAFPTGCSLNCVAAHWTPNGGDKTVLQYDDVMKLDFGTHINGYIVDSAFTVAF 253
Orysa_AK122063        ------GIAFPTGCSLNWVAAHWTPNSGDKTVLQYDDVMKLDFGTHIDGYIVDCAFTVAF 241
Zeama_AY105027        ------GIAFPTGCSLNWVAAHWTPNAGDKTVLQYDDVMKLDFGTHIDGYIVDCAFTVAF 239
RatMetAP2             ------GLAFPTGCSLNNCAAHYTPNAGDTTVLQYDDICKIDFGTHISGRIIDCAFTVTF 269
MouseMetAP2           ------GLAFPTGCSLNNCAAHYTPNAGDTTVLQYDDICKIDFGTHISGRIIDCAFTVTF 269
humanMetAP2           ------GLAFPTGCSLNNCAAHYTPNAGDTTVLQYDDICKIDFGTHISGRIIDCAFTVTF 269
drosophilaMetAP2      ------GLAFPTGCSLNHCAAHYTPNAGDPTVLQYDDVCKIDFGTHIKGRIIDCAFTLTF 239
YeastMetAP2           EDPKSQGIGFPTGLSLNHCAAHFTPNAGDKTVLKYEDVMKVDFGVHVNGRIVDSAFTVSF 212
Orysa_AK107616        DNLLG-GVAFPTGLSINHCAAHYTPNAGNKMTLKQEDVMKVDPGVHVNGRIVDSAFTVAF 234
Arath_MAP1A           ----YYFFPKSCCTSVNEVICHGIP---DARKLEDGDIVNVDVTVCYKGCHGDLNETYFV 249
human_MAP1            ----YYNFPKSCCTSVNEVICHGIP---DRRPLQEGDIVNVDITLYRNGYHGDLNETFFV 124
yeast_MAP1            ----YYNFPKSLCTSVNEVICHGVP---DKTVLKEGDIVNLDVSLYYQGYHADLNETYYV 237
Arath_MAP1B           ----YGGFPKSVCTSVNECMCHGIP---DSRQLQSGDIINIDVTVYLDGYHGDTSRTFFC 234
Arath_MAP1C           ----YGGFPKSVCTSVNECMFHGIP---DSRPLQNGDIINIDVAVYLDGYHGDTSKTFLC 207
Arath_MAP1D           ----YGGFPKSVCTSVNECICHGIP---DSRPLEDGDIINIDVTVYLNGYHGDTSATFFC 215
                                                                            PEPTI -
                                                                            MAP1 signature
Arath_MAP2A_CDS0431   NPMFDPLLAASRDATYTGIKEAGVDVRLCDVGAAVQEVMESYEVEINGKVYQVKSIRNLN 291
AtMAP2B_CDS0430       NPMFDPLLAASREATYTGIKEAGIDVRLCDIGAAIQEVMESYEVEINGKVFQVKSIRNLN 290
oryza_BAD03108        NPMFDPLLQASRDATNAGVKEAGIDARLCDVGAAIQEVMESYEVEINGKVFQVKSVRNLN 313
Orysa_AK122063        NPMFDSLLQASKDATNTGVKEAGIDARLCDVGAAIQEVMESYEVEINGKVFQIKSVRNLN 301
Zeama_AY105027        NPMFDPLLQATRDATNTGIKEAGIDARLGDVGAAIQEVMESYEVEINGKVFQVKSVRNLN 299
RatMetAP2             NPKYDILLKAVKDATNTGIKCAGIDVRLCDVGEAIQEVMESYEVEIDGKTYQVKPIRNLN 329
MouseMetAP2           NPKYDILLTAVKDATNTGIKCAGIDVRLCDVGEAIQEVMESYEVEIDGKTYQVKPIRNLN 329
humanMetAP2           NPKYDTLLKAVKDATNTGIKCAGIDVRLCDVGEAIQEVMESYEVEIDGKTYQVKPIRNLN 329
drosophilaMetAP2      NNKYDKLLQAVKEATNTGIREAGIDVRLCDIGAAIQEVMESYEIELDGKTYPIKAIRNLN 299
YeastMetAP2           DPQYDNLLAAVKDATYTGIKEAGIDVRLTDIGEAIQEVMESYEVEINGETYQVKPCRNLN 272
Orysa_AK107616        EPRYDPLLAAVKDATNTGIRLAGIDARLGEIGEGIQEAMESYEVELDGKVHPVKCIRNLN 294
Arath_MAP1A           GN-VDEASRQLVKCTYECLEKA---IAIVKPGVRFEIGE--IVNRHATMSGLSVVRSYC  303
human_MAP1            GE-VDDGARKLVQTTYECLMQA---IDAVKPGVRYRELGN--IIQKHAQANGFSVVRSYC  178
yeast_MAP1            GENISKEALNTTETSRECLKLA---IKMCKPGTTFQELGD--HIEKHATENKCSVVRTYC  292
Arath_MAP1B           GE-VDEGFKQLVKVTEECLEKG---IAVCKDGASFKKIGK--RISEHAEKFGYNVVERFV  288
Arath_MAP1C           GD-VNGSLKQLVKVTEECLEKG---ISVCKDGASFKQIGK--IISEBHAAKYGYN-MERFI 260
Arath_MAP1D           GN-VDEKAKKLVEVTKESLDKA---ISICGPGVEYKKIGK--VIHDLADKHKYGVVRQFV  269
```

FIGURE 3B

|  | PEPTIDASE DOMAIN | M24 |
|---|---|---|

| | MAP1 signature | |
|---|---|---|
| Arath_MAP2A_CDS0431 | GHSIGRYQIHA---EKSVPNVRGG--EQTKMEEGELYAIETFGSTGKGYVREDLECSHYM | 346 |
| AtMAP2B_CDS0430 | GHSIGPYQIHA---GKSVPIVKGG--EQTKMEEGEFYAIETFGSTGKGYVREDLECSHYM | 345 |
| oryza_BAD03108 | GHGIGPYQIHF---GKSVPVVKGG--EQTKMEEGEFYAIETFGSTGKGFVREDLECSHYM | 368 |
| Orysa_AK122063 | GHSIGPYQIHA---GKSVPIVKGG--EQTKMEEGEFYAIETFGSTGKGFVREDLECSHYM | 356 |
| Zeama_AY105027 | GHSIGPYQIHA---GKSVPIVKGG--EQTKMEEGEFYAIETFGSTGKGFVREDLECSHYM | 354 |
| RatMetAP2 | GHSIGPYRIHA---GKTVPIVKGG--EATRMEEGEVYAIETFGSTGKGVVHDDMECSHYM | 384 |
| MouseMetAP2 | GHSIGPYRIHA---GKTVPIVKGG--EATRMEEGEVYAIETFGSTGKGVVHDDMECSHYM | 384 |
| humanMetAP2 | GHSIGQYRIHA---GKTVPIVKGG--EATRMEEGEVYAIETFGSTGKGVVHDDMECSHYM | 384 |
| drosophilaMetAP2 | GHSISPYRIHA---GKTVPIVKGG--ESTRMEEDEFYAIETFGSTGRGLVHDDMDCSHYM | 354 |
| YeastMetAP2 | GHSIAPYRIHG---GKSVPIVKNG--DTTKMEEGEHFAIETFGSTGRGYVTAGGEVSHYA | 327 |
| Orysa_AK107616 | GHTISQYSIHCGSACKSVPIVKSA--TTEKMEEGEVYAIETFGSTGKGYVHEDMGCSHYA | 352 |
| Arath_MAP1A | GHGIGDLFHCA----PNIPHYARN-KAVGVMKAGQTFTIEPMINAGG------------- | 345 |
| human_MAP1 | GHGIHKLFHTA----PNVPHYAKN-KAVGVMKSGHVFTIEPMICEGG------------- | 220 |
| yeast_MAP1 | GHGVGEFFHCS----PNIPHYAKN-RTPGVMKPGMVFTIEPMINEGT------------- | 334 |
| Arath_MAP1B | GHGVGPVFHSE----PLIYHYRND--EPGLMVEGQTFTIEPILTIGT------------- | 329 |
| Arath_MAP1C | GHGLGTVLHSE----PLIYLHSNYDYELEYMIEGQTFTLEPILTIGT------------- | 303 |
| Arath_MAP1D | GHGVGSVFHAD----PVVLHFRNN--EAGRMVLNQTFTIEPMLTIGS------------- | 310 |

| - PEPTIDASE DOMAIN | M24 | |
|---|---|---|

| | | |
|---|---|---|
| Arath_MAP2A_CDS0431 | KNYDVGHVPLRLPRAKQLLATINKNFSTLAFCRRYLDRLGETKYLMALKNLCDSGIIEPC | 406 |
| AtMAP2B_CDS0430 | KNFDAGHVPLRLPRAKQLLATINKNFSTLAFCRRYLDRIGETKYLMALKNLCDSGIVQPY | 405 |
| oryza_BAD03108 | KNFDVGHVPLRAAKAKQLLVTINNNFGTLAFCRRYLDRLGETKYLMALKNLCDAGIVEPC | 428 |
| Orysa_AK122063 | KNFDVGHVPLRVAKAKQLLGTINNNFGTLAFCRRYLDRLGETKYLMALKNLCDVGIVQPY | 416 |
| Zeama_AY105027 | KNFDVGHVPLRLAKAKQLLGTINHNFGTLAFCRRYL------------------------ | 390 |
| RatMetAP2 | KNFDVGHVPIRLPRTKHLLNVINENFGTLAFCRRWLDRLGESKYLMALKNLCDLGIVDPY | 444 |
| MouseMetAP2 | KNFDVGHVPIRLPRTKHLLNVINENFGTLAFCRRWLDRLGESKYLMALKNLCDLGIVDPY | 444 |
| humanMetAP2 | KNFDVGHVPIRLPRTKHLLNVINENFGTLAFCRRWLDRLGESKYLMALKNLCDLGIVDPY | 444 |
| drosophilaMetAP2 | KNFDLPFVPLRLQSSKQLLGTINKNFGTLAFCKRWLDRAGATKYQMALKDLCDKGIVEAY | 414 |
| YeastMetAP2 | RSAEDHQVMPTLDSAKNLLKTIDRNFGTLPFCRRYLDRLGQEKYLFALNNLVRHGLVQDY | 387 |
| Orysa_AK107616 | KIDDAPKVALRVQSAKTLLRTIEKNFGTLPFCRRYLDRLGHDKYLLGLNNLVQSGIVQDY | 412 |
| Arath_MAP1A | -----------------------WRDRTWPDGWTAVTAD----------------- | 361 |
| human_MAP1 | -----------------------WQDETWPDGWTAVTRD----------------- | 236 |
| yeast_MAP1 | -----------------------WKDMTWPDDWTSTTQD----------------- | 350 |
| Arath_MAP1B | -----------------------TECVTWPDNWTTLTAD----------------- | 345 |
| Arath_MAP1C | -----------------------TEFVTWPDKWTIVTAD----------------- | 319 |
| Arath_MAP1D | -----------------------RNPIMWDDNWTVVTED----------------- | 326 |

| | | |
|---|---|---|
| Arath_MAP2A_CDS0431 | PPVCDVKGSYISQFEHTILLRPTCKEIISKGDDY---------- | 440 |
| AtMAP2B_CDS0430 | PPLCDVKGSYVSQFEHTILLRPTCKEVLSKGDDY---------- | 439 |
| oryza_BAD03108 | PPMCDVRGSYVSQSEHTILLRPTCKEVISRGDDY---------- | 462 |
| Orysa_AK122063 | PPLCDVRGSYVSQFEHTILLRPTCKEVISRGDDY---------- | 450 |
| Zeama_AY105027 | -------------------------------------------- | |
| RatMetAP2 | PPLCDIKGSYTAQFEHTILLRPTCKEVVSRGDDY---------- | 478 |
| MouseMetAP2 | PPLCDIKGSYTAQFEHTILLRPTCKEVVSRGDDY---------- | 478 |
| humanMetAP2 | PPLCDIKGSYTAQFEHTILLRPTCKEVVSRGDDY---------- | 478 |
| drosophilaMetAP2 | PPLCDIKGCYTAQYEHTIMLRPTCKEVVSKGDDY---------- | 448 |
| YeastMetAP2 | PPLNDIPGSYTAQFEHTILLHAHKKEVVSKGDDY---------- | 421 |
| Orysa_AK107616 | PPLVDVKGSYTAQYEHTILLRPNVKEVVSRGDD----------- | 445 |
| Arath_MAP1A | -------GKRSAQFEHTLLVTETGVEVLTARLPSS-PDVYPWLTK | 398 |
| human_MAP1 | -------GKRSAQFEHTLLVTDTGCEILTRRLDSARPHFMSQF-- | 272 |
| yeast_MAP1 | -------GKLSAQFEHTLLVTEHGVEILTARNKKSPGGPRQRIK- | 387 |
| Arath_MAP1B | -------GGVAAQFEHTILITRTGSEILTKC-------------- | 369 |
| Arath_MAP1C | -------GGPAAQFEHTILITTTGAEILTISS------------- | 344 |
| Arath_MAP1D | -------ASLSAQFEHTILITKDGAEILTKC-------------- | 350 |

FIGURE 3C

US 7,919,678 B2

METHOD FOR MODIFYING PLANT GROWTH CHARACTERISTICS

This application is the US national phase of international application PCT/EP2004/050092 filed 6 Feb. 2004, which designated the U.S. and claims benefit of EP 03075363.6, filed 6 Feb. 2003, the entire contents of each of which are hereby incorporated by reference.

The present invention concerns a method for modifying plant growth characteristics. More specifically, the present invention concerns a method for modifying plant growth characteristics by modifying expression of a nucleic acid encoding a methionine aminopeptidase (MAP protein) and/or by modifying level and/or activity of a MAP protein in a plant. The present invention also concerns plants having modified expression of a nucleic acid encoding a MAP protein and/or modified level and/or activity of a MAP protein, which plants have modified growth characteristics relative to corresponding wild type plants.

Given the ever-increasing world population, it remains a major goal of agricultural research to improve the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. In contrast, advances in molecular biology have allowed mankind to more precisely manipulate the germplasm of plants. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits, for example improved yield.

The ability to influence one or more of the plant growth characteristics, would have many applications in areas such as crop enhancement, plant breeding, production of ornamental plants, arboriculture, horticulture, forestry, production of algae or plants (for use as bioreactors for example, for the production of pharmaceuticals such as antibodies or vaccines, or for the bioconversion of organic waste, or for use as fuel in the case of high-yielding algae and plants).

It has now been found that modifying expression in a plant of a nucleic acid encoding a MAP protein, and/or modifying in a plant level and/or activity of a MAP protein, gives plants having modified growth characteristics.

Accordingly, the present invention provides a method for modifying plant growth characteristics relative to corresponding wild type plants, comprising modifying expression in a plant of a nucleic acid encoding a methionine aminopeptidase (MAP) protein and/or modifying level and/or activity in a plant of a MAP protein.

The term "modifying" as used herein is taken to mean increasing, decreasing and/or changing in place and/or time. Modifying expression of a nucleic acid encoding a MAP protein or modifying level and/or the activity of a MAP protein encompasses altered expression of a gene and/or altered level and/or activity of a gene product namely a polypeptide, in specific cells or tissues, when compared to expression, level and/or activity of a MAP gene or protein in corresponding wild-type plants. The modified gene expression may result from modified expression of an endogenous MAP gene and/or may result from modified expression of a MAP gene previously introduced into a plant. Similarly, modified levels and/or activity of a MAP protein may be due to modified expression of an endogenous MAP nucleic acid or protein and/or due to modified expression of a MAP nucleic acid or protein previously introduced into a plant. Modified expression of a nucleic acid/gene and/or modified level and/or activity of a gene product/protein may be effected, for example, by chemical means and/or recombinant means.

According to a preferred embodiment of the present invention, modifying expression of a nucleic acid encoding a MAP protein and/or modifying level and/or activity of a MAP protein may be effected by recombinant means. Such recombinant means may comprise a direct and/or indirect approach.

For example, an indirect recombinant approach may comprise introducing, into a plant, a nucleic acid capable of modifying expression of a MAP gene and or capable of modifying level and/or activity of a MAP protein. Examples of such nucleic acids to be introduced into a plant include nucleic acids encoding transcription factors or activators or inhibitors that bind to the promoter of a MAP gene or that interact with a MAP protein. Methods to test these types of interactions and methods for isolating nucleic adds encoding such interactors include yeast one-hybrid or yeast two-hybrid screens in which the MAP gene/protein is used as bait. Therefore, modifying expression of a nucleic acid encoding a MAP protein and/or modifying level and/or activity of the MAP protein may be effected by decreased or increased levels of factors that control expression of the MAP gene or that directly or indirectly (in)activate the MAP protein. Further, modifying level and/or activity of a MAP protein may be effected by modifying levels of a factor capable of interacting with a MAP protein. Such factors may include a ligand or a natural target/substrate of a MAP protein. An example of such a target includes the eukaryotic initiation factor eIF2, which is part of the protein translation initiation complex.

Also encompassed by an indirect recombinant approach for modifying expression of a MAP gene and/or modifying level and/or activity of a MAP protein is the provision of, or the inhibition or stimulation of regulatory elements that drive expression of MAP gene, for example the endogenous MAP gene. For example, such regulatory elements to be introduced into a plant may be a promoter capable of driving expression of an endogenous MAP gene.

A preferred recombinant approach for modifying expression of a nucleic acid encoding a MAP protein and/or modification of level and/or activity of a MAP protein comprises introducing into a plant a nucleic acid capable of modifying expression of a nucleic acid encoding a MAP protein and/or capable of modifying level and/or activity of a MAP protein.

Accordingly, the present invention provides a method for modifying plant growth characteristics as described above, wherein the modifying expression, level and/or activity is effected by introducing into a plant a nucleic acid capable of modifying expression of a nucleic acid encoding a MAP protein and/or capable of modifying level and/or activity of a MAP protein. According to a more direct and further preferred embodiment of such a method, that nucleic acid is a nucleic acid encoding a MAP protein or a variant thereof as described herein below, or is a variant of a nucleic acid encoding a MAP protein. This nucleic acid encoding a MAP protein may be wild type, i.e. the native or endogenous. Alternatively, the nucleic acid may be heterologous, i.e. derived from the same or another species, which nucleic acid is introduced as a transgene. This transgene may be substantially modified from its native form in composition and/or genomic environment through deliberate human manipulation.

Additionally or alternatively, modifying expression of the nucleic acid encoding a MAP protein and/or modifying level and/or activity of the MAP protein itself may be effected by a chemical approach. Such a chemical approach may involve exogenous application of one or more compounds or elements capable of modifying expression of a MAP nucleic acid (endogenous gene or introduced into the plant) and/or capable of modifying level and/or activity of a MAP protein (endogenous or introduced into the plant). The term "exogenous application" as defined herein is taken to mean the contacting or administering of a suitable compound or element to a plant, plant cell, tissue or organ. The compound or element may be exogenously applied to a plant in a form suitable for plant uptake (such as through application to the soil for uptake via the roots, or in the case of some plants, by applying directly to the leaves, for example by spraying). The exogenous application may take place on wild-type plants or on transgenic plants that have previously been transformed with a MAP nucleic acid/gene or other transgene.

Suitable compounds or elements for exogenous application include MAP proteins or MAP nucleic acids. Alternatively, suitable compounds or elements include those capable of directly or indirectly binding or (in)activating a MAP protein. Suitable compounds also include antibodies that can recognise or mimic the function of a MAP protein. Such antibodies may comprise "plantibodies", single chain antibodies, IgG antibodies and heavy chain camel antibodies, as well as fragments thereof. Other suitable compounds or elements for chemical modification of expression, activity and/or level of a MAP gene or protein, include mutagenic substances, such as N-nitroso-N-ethylurea, ethylene imine, ethyl methanesulphonate and diethyl sulphate. Mutagenesis may also be achieved by exposure to ionising radiation, such as X-rays or gamma-rays or ultraviolet light. Methods for introducing mutations, and for testing the effect of mutations (such as by monitoring gene expression and/or protein activity), are well known in the art.

Therefore, according to one aspect of the present invention, there is provided a method for modifying plant growth characteristics, comprising exogenous application of one or more compounds or elements capable of modifying expression of a MAP gone and/or capable of modifying level and/or activity of a MAP protein.

Methionine aminopeptidases (MetAP or MAP) are described in literature to be responsible for removal of the initiator methionine residue of a peptide during protein synthesis (Bradshaw and Yi, 2002, Essays Biochem 38:65-78). Methionine aminopeptidases are specific and ubiquitous enzymes that belong to the family of metalloenzymes. It has been found that Eukaryotes have two classes of methionine aminopeptidase (MAP1 and MAP2), while prokaryotes only have one. MAP2 is also known as the eukaryotic initiation factor 2 alpha (eIF2alpha) associated protein p67. It has been demonstrated that rat p67 In addition to its peptidase function, also plays an important role in translational regulation by preventing the phosphorylation of the alpha subunit of initiation factor-2. Accordingly, MAP2 proteins have, in addition to their peptidase activity, a non-proteolytic function to protect eIF2alpha against phosphorylation (POEP), which eIF2alpha is inactive in the phosphorylated state (Datta R et al. Biochimie. 2001 83:919-31). MAP proteins from various organisms have been studied with respect to their function as well as their structure. Based on sequence analysis, MAP proteins have been found to have a MAP signature and a peptidase domain. For example, typical structural features of a MAP1 protein are a MAP1 signature (PROSITE PS00680= [MFY]-x-G-H-G-[LIVMC]-[GSH]-x(3pH-x(4)-[LIVM]-x-[HN]-[YWVH]) and a pFAM PEPTIDASE_M24 domain. Typical structural features of a MAP2 protein include a MAP2 signature (PROSITE PS01202=[DA]-[LIVMY]-x-K-[LIVM]-D-x-G-x-[HQ]-[LIVM]-[DNS]-G-x(3)-[DN]) and a pFAM PEPTIDASE_M24 domain. MAP2 proteins, such as plant MAP2 proteins, additionally comprise at least one lysine-rich domain at the N-terminus. MAP proteins isolated from yeast have been described in Li and Chang, (1995) Proc Natl Acad Sci. USA. 92(26): 12357-61, Human MAP proteins have been described in Li and Chang (1996) Biochem Biophys Res Commun 227:152-159 and six MAP cDNAs were cloned from *Arabidopsis thaliana* and corresponding proteins were characterized in vivo and in vitro (Giglione et al. EMBO J. 2000 19:5916-29). One example of an *Arabidopsis thaliana* MAP protein is herein represented by SEQ ID NO 2, and its encoding sequence by SEQ ID NO 1. Another example of an *Arabidopsis thaliana* MAP protein is herein represented by SEQ ID NO 4, and its encoding sequence by SEQ ID NO 3.

The term "MAP protein" as used herein encompasses a methionine aminopeptidases (MAP), for example a MAP of SEQ ID NO 2 or 4, as well as a variant thereof (or a proteins essentially similar thereto). The terms "MAP gene" or "MAP nucleic acid" or "nucleic acid encoding a MAP protein" are used herein interchangeably and also encompass variant MAP nucleic acids, for example variants of SEQ ID NO 1 or 3. The terms "a variant of" and "essentially similar to" are used interchangeably herein. Variant MAP proteins or variant nucleic acids encoding a MAP protein include:

(i) Functional portions of a MAP nucleic acid, for example a MAP nucleic acid of SEQ ID NO 1 or 3;
(ii) Sequences capable of hybridising with a MAP nucleic acid, for example with a MAP nucleic acid of SEQ ID NO 1 or 3;
(iii) Alternative splice variants of a MAP nucleic acid, for example a MAP nucleic acid of SEQ ID NO 1 or 3;
(iv) Allelic variants of a MAP nucleic acid, for example a MAP nucleic acid of SEQ ID NO 1 or 3; and
(v) Homologues, derivatives and active fragments of a MAP protein, for example a MAP protein of SEQ ID NO 2 or 4.

Advantageously, the methods according to the invention may be practised using variant MAP proteins and variant MAP nucleic acids. Suitable variants include variants of SEQ ID NO 2 or 4 and/or variants of SEQ ID NO 1 or 3. However, it should be clear that the applicability of the invention is not limited to the use of the nucleic acid represented by SEQ ID NO 1 or 3, nor to the nucleic acid encoding the amino acid sequence represented by SEQ ID NO 2 or 4, but that other nucleic acids encoding variants of SEQ ID NO 2 may be useful in the methods of the present invention.

For use in the methods according to the present invention, the MAP protein preferably comprises any one or both of the following domains:
a) a MAP signature
b) a peptidase_M24 domain A preferred MAP protein comprises both of these domains in the above rank order.

The term "variant" also includes variants in the form of a complement, DNA, RNA, cDNA or genomic DNA. The variant nucleic acid may be synthesized in whole or in part, it may be a double-stranded nucleic acid or a single-stranded nucleic acid. Also, the term "variant" encompasses a variant due to the degeneracy of the genetic code; a family member of the gene or protein; and variants that are interrupted by one or more intervening sequences such as introns or transposons.

One variant nucleic acid encoding a MAP protein is a functional portion of a nucleic acid encoding a MAP protein. Advantageously, the method of the present invention may also be practised using portions of a nucleic acid encoding a MAP protein. A functional portion refers to a piece of DNA derived from or prepared from an original (larger) DNA molecule, which portion, retains at least part of the functionality of the original, DNA and which, when expressed in a plant, gives plants having modified growth characteristics. The portion may comprise many genes, with or without additional control elements or may contain spacer sequences. The portion may be made by making one or more deletions and/or truncations to the nucleic acid. Techniques for introducing truncations and deletions into a nucleic acid are well known in the art. Portions suitable for use in the methods according to the invention may readily be determined by following the methods described in the Examples section by simply substituting the sequence used in the actual Example with the portion to be tested for functionality.

Another variant of a nucleic acid encoding a MAP protein is a nucleic acid capable of hybridising with a nucleic acid encoding a MAP protein, for example to any of the nucleic acids encoding a protein represented by SEQ ID NO 2 or 4. Hybridising sequences suitable for use in the methods according to the invention may readily be determined, for example by following the methods described in the Examples section by simply substituting the sequence used in the actual Example with the hybridising sequence.

The term "hybridising" as used herein means annealing to a substantially homologous complementary nucleotide sequences in a hybridization process. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, sodium/salt concentration and hybridisation buffer composition. High stringency conditions for hybridisation include high temperature and/or low salt concentration (salts include NaCl and $Na_3$-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid. Sufficiently low stringency hybridisation conditions are particularly preferred (at least in the first instance) to isolate nucleic acids heterologous to the DNA sequences of the invention defined supra. An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed, such as medium stringency conditions. Examples of medium stringency conditions include 1-4×SSC/0.25% w/v SDS at ≧45° C. for 2-3 hours. With specifically hybridising is meant hybridising under stringent conditions. An example of high stringency conditions includes 0.1-2×SSC, 0.1×SDS, and 1×SSC, 0.1× SDS at 60° C. for 2-3 hours.

The methods according to the present invention may also be practised using an alternative splice variant of a nucleic acid encoding a MAP protein, for example an alternative splice variant of SEQ ID NO 1 or 3. The term "alternative splice variant" as used herein encompasses variants of a nucleic acid in which selected introns and/or exons have been excised, replaced or added. Such splice variants may be found in nature or may be manmade. Methods for making such splice variants are well known in the art. Splice variants suitable for use in the methods according to the invention may readily be determined, for example, by following the methods described in the Examples section by simply substituting the sequence used in the actual Example with the splice variant.

Another variant MAP nucleic acid useful in practising the method for modifying plant growth characteristics, is an allelic variant of a MAP gene, for example an allelic variant of SEQ ID NO 1 or 3. Allelic variants exist in nature and encompassed within the methods of the present invention is the use of these natural alleles. Allelic variants also encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms. Allelic variants suitable for use in the methods according to the invention may readily be determined for example by following the methods described in the Examples section by simply substituting the sequence used in the actual Example with the allelic variant.

The present invention provides a method for modifying plant growth characteristics, comprising modifying expression in a plant of an alternative splice variant or of an allelic variant of a nucleic acid encoding a MAP protein and/or by modifying level and/or activity in a plant of a MAP protein encoded by an alternative splice variant or allelic variant.

One example of a variant MAP protein useful in practising the methods of the present invention is a homologue of a MAP protein. "Homologues" of a particular MAP protein encompass peptides, oligopeptides, polypeptides, proteins and enzymes having an amino acid substitution, deletion and/or insertion relative to that particular MAP protein and having similar biological and functional activity as a MAP protein. Homologues of a MAP proteins may be manmade via the techniques of genetic engineering and/or protein engineering. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

Additionally and/or alternatively, homologues of a particular MAP protein exist in nature and may be found in the same or different species or organism from which the particular MAP protein is derived. Two special forms of homologues, orthologues and paralogues, are evolutionary concepts used to describe ancestral relationships of genes. The term "orthologues" relates to homologous genes in different organisms due to ancestral relationship. The term "paralogues" relates to gene-duplications within the genome of a species leading to paralogous genes. The term "homologues" of a MAP protein as used herein therefore encompasses paralogues and orthologues of the MAP protein, which are also useful for practising the methods of the present invention.

The homologues useful in the method according to the invention have, in increasing order of preference, at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 58%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the sequence of SEQ ID NO 2 or with the sequence of SEQ ID NO 4, preferably over the full length of SEQ ID NO 2 or 4.

The percentage of sequence identity is calculated using a pairwise global alignment program implementing the algorithm of Needleman-Wunsch (J. Mol. Biol. 48: 443-453, 1970) which maximizes the number of matches and minimizes the number of gaps. For calculation of the above-mentioned percentages, the program Align X (as part of the Vector NTI suite 5.5) is used with the standard parameters and the variable parameters gap opening penalty 10 and gap extension penalty 0.1.

Multiple alignment of MAP proteins from various sources is generated using the program Clustal X with the standard fixed parameters and the variable parameters Gap opening penalty 10 and Gap extension penalty 0.2. Percentage of identity between the proteins of this multiple alignment was calculated using the BoxShade software (available at URL: isrec.isb-sib.ch/ftp-server/boxshade). Table I gives an overview of these percentages.

TABLE I

Sequence identity between different MAP proteins

| General | % identity | Sequences used for calculation |
|---|---|---|
| Between MAP2 of dicots | 90% | 2 *Arabidopsis* sequences |
| Between MAP2 of monocots | 80% | 2 rice and 1 maize sequences |
| Between MAP2 of dicots and monocots | 76% | 3 monocot and 2 dicot sequences |
| Between MAP2 of plants and animals | 65% | 5 plant and 4 animal sequences |
| Between MAP1 and MAP2. | 20% | 11 MAP2 and 6 MAP1 sequences |

The homologues useful in the methods according to the invention may be derived (either directly or indirectly, i.e. if subsequently modified) from any source provided that the sequence, when expressed in a plant, leads to modified growth characteristics. The nucleic acid may be isolated from a microbial source, such as bacteria, yeast or fungi, or from a plant, algae, insect or animal (including human) source.

The nucleic acid encoding a MAP homologue is preferably isolated from a plant. Further preferably, the nucleic acid is isolated from a dicotyledoneous plant, preferably from the family Bressicaceae, further preferably from *Arabidopsis thaliana*. MAP proteins of *Arabidopsis* have been subdivided into different classes on the basis of their level of sequence homology (Giglione et al. (2000, EMBO J. 19: p 5916-5929). Class MAP1 (with A, B, C and D isoforms) and class MAP2 (with A and B isoforms) were identified in *Arabidopsis*. These classes and isoforms are also encompassed by the term "homologue" as used herein. Advantageously, these different classes or isoforms of MAP proteins, or their encoding nucleic acids, may be used in the methods of the present invention. Accordingly, the present invention provides a method as described hereinabove, wherein the MAP nucleic acid or MAP protein is obtained from a plant, preferably from a dicotyledoneous plant, further preferably from the family Brassicaceae, more preferably from *Arabidopsis thaliana*. According to a further embodiment, a MAP nucleic acid or protein is a MAP2 nucleic acid or protein or a MAP1 nucleic acid or protein. According to a further embodiment of the invention, the MAP nucleic acid encodes or the MAP protein is, an isoform of the MAP protein represented by SEQ ID NO 2 or 4. According to a further embodiment of the invention, the MAP nucleic acid encodes or the MAP protein is the *Arabidopsis thaliana* MAP2B protein represented by SEQ ID NO 2.

Other preferred MAP homologues and their encoding sequences may be found in (public) sequence databases. Methods for the search and identification of MAP homologues in sequence databases would be well within the realm of persons skilled in the art. Such methods, involve screening sequence databases with the sequences provided by the present invention, for example SEQ ID NO 2 or 4 (or SEQ ID NO 1 or 3), preferably in a computer readable form. Useful sequence databases include, but are not limited, to Genbank (URL: ncbi.nlm.nih.qov/web/Genbank), the European Molecular Biology Laboratory Nucleic acid Database (EMBL) (URL: w.ebi.ac.uk/ebi-docs/embl-db.html)or versions thereof or the MIPS database (URL: mips.gsf.de). Different search algorithms and software for the alignment and comparison of sequences are well known in the art. Such software includes for example GAP, BESTFIT, BLAST, FASTA and TFASTA. Preferably the BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1: 543, 1997). The software for performing BLAST analysis is publicly available through the National Centre for Biotechnology Information.

Orthologues of a MAP protein in other plant species may easily be found by performing a reciprocal Blast search. This method encompasses searching one or more sequence databases with a query gene or protein of interest (for example SEQ ID NO 1, 2, 3 or 4), using for example the BLAST program. The highest-ranking subject genes that result from the search are then used as a query sequence in a similar BLAST search. Only those genes that have as a highest match again the original query sequence (SEQ ID NO 1, 2, 3 or 4) are considered to be orthologous genes. For example, to find a rice orthologue of an *Arabidopsis thaliana* gene, one may perform a BLASTN or TBLASTX analysis on a rice database such as (but not limited to) the *Oryza sativa Nipponbare* database available at the NCBI website (URL: ncbi.nlm.nih.gov) or the genomic sequences of rice (cultivars indica or japonica). In a next step, the obtained rice sequences are used in a reverse BLAST analysis using an *Arabidopsis* database. The method can be used to identify orthologues from many different species, for example from corn.

Paralogues of a MAP protein in the same species may easily be found by performing a Blast search on sequences of the same species from which the MAP protein is derived. From the sequences that are selected by the Blast search, the true paralogues may be identified by looking for identity between the sequences or for conservation of typical MAP domains. A search for paralogues of the *Arabidopsis thaliana* MAP protein has been carried out by Giglione et al. (2000, EMBO J. 19: p 5916-5929).

A BLAST using default parameters and using SEQ ID NO 2 or SEQ ID NO 1 as search sequence was performed and resulted in the identification of the following MAP nucleic acids and proteins. Sequences substantially identical to SEQ ID NO 1 (AtMAP2B) have been published under Genbank accession numbers NM-115862 (genomic DNA), BT000063 (At3g59990 mRNA), AY084710, AY065161 and AF300B80. One isoform of SEQ ID NO 1 and 2, named herein AtMAP2A, was found in the database under Genbank accession number AF250964. Isoforms of a different dass were found in the database under Genbank accession numbers AF250960 ((AtMAP1A and represented herein by SEQ ID NO 3 and SEQ ID NO 4), AF250961 (AtMAP1B), AF250962 (AtMAP1C) and AF250963 (AtMAP1D).

Also MAP homologues from different plant species have been identified, which homologues are useful in the methods of the present invention. There is a high degree of conservation among the MAP proteins of plants (see Table I). Such homologues include for example, the MAP protein from *Oryza sativa* as published in Genbank database under accession number BAD03108, the *Oryza sativa* protein under accession number AK122063, the *Oryza sativa* protein under Genbank accession number AK107616 and the *Zee Mays* protein under Genbank accession number AY105027. The genes encoding MAP homologues of crop plants may be especially useful in practising the methods of the invention in crop plants. In another embodiment of the invention, the genes encoding MAP homologues of a dicot plant may be used to practise the methods of the present invention in a monocot plant, or vice versa.

The genome sequences of *Arabidopsis thaliana* and *Oryza sativa* are now available in public databases such as Genbank and other genomes are currently being sequenced. Therefore, it is expected that further homologues will readily be identifiable by sequence alignment with SEQ ID NO 1 or 3 or with SEQ ID NO 2 or 4 using the programs Blast X or BlastP or other programs.

A phylogenetic tree may be constructed with all the homologues, paralogues and orthologues as defined hereinabove. Multiple alignments are made using the program ClustalX as described hereinabove. The phylogenetic tree is made by the Phylip software package available at http://evolution.genetics.washington.edu/phylip.html. Sequences clustering around one or more of the 6 MAP proteins of *Arabidopsis thaliana* identify proteins, and their corresponding genes, suitable for use in the methods of the present invention.

The above-mentioned software analyses for comparing sequences, for the calculation of sequence identity, for the search for homologues, orthologues or paralogues or for the making of a phylogenetic tree, is preferentially done with full-length sequences. Alternatively, these software analyses may be carried out on with a conserved region of the MAP protein or DNA sequence. Accordingly, these analyses may be based on the comparison and calculation of sequence identity between conserved regions, functional domains, motifs or boxes.

The identification of such domains or motifs, for example, the domains represented by SEQ ID NO 5 (MAP1 signature), SEQ ID NO 6 (MAP2 signature), SEQ ID NO 7 (peptidase_M24 domain of AtMAP1A), SEQ ID NO 8 (peptidase_M24 domain of AtMAP2B), SEQ ID NO 9 (lysine-rich domain of AtMAP2B), would also be well within the realm of a person skilled in the art and involves screening a computer readable format of MAP proteins for the presence of conserved protein domains, motifs and boxes. Protein domain information is available in the PRODOM URL: biochem.ucl.ac.uk/bsm/dbbrowser/jj/prodomsrchjj.html), PIR URL: pir.georgetown.edu/), PROSITE (http://au.expasy.org/PROSITE/) or pFAM (http://pFAM .wustl.edu/) database. Software programs designed for such domain searching include, but are not limited to, MotifScan, MEME, SIGNALSCAN, and GENESCAN. MotifScan is a preferred software program and is available at URL: hits.isb-sib.ch/cgi-bin/PFSCAN, which program uses the protein domain information of PROSITE and pFAM . A MEME algorithm (Version 3.0) may be found in the GCG package; or at URL: www.sdsc.edu/MEME/meme. SIGNALSCAN version 4.0 information is available at URL: biosci.cbs.umn.edu/software/sigscan.html. GENESCAN may be found at URL: gnomic.stanford.edu/GENESCANW.html.

The term "MAP signature" means a MAP-specific domain. Examples of such MAP signatures are MAP1 or MAP2 signatures. The MAP1 signature is described in the PROSITE database under accession number PS00680 and is herein represented by the consensus sequence of SEQ ID NO 5: [MFY]-x-G-H-G-[LIVMC]-[GSH]-x(3)-H-x(4)-[LIVM]-x-[HN]-[YWVH]. In MAP1 proteins, the MAP1 signature may be located within the peptidase domain. The MAP2 signature is further described in the PROSITE database under accession number PS01202 and is herein represented by the consensus sequences of SEQ ID NO 6: [DA]-[LIVMYFx-K-[LIVM]-D-x-G-x-[HQ]-[LIVM]-[DNS]-G-x(3)-[DN]. In case of MAP2 proteins, the MAP2 signature is preferably located upstream of the peptidase domain. A person skilled in the art will recognize that a MAP signature may deviate, with for example 1 or 2 mismatches, from the above-mentioned consensus MAP signatures, without loosing its functionality. One example is found in the *Drosophila* MAP2 protein (see FIGS. 3A-3C), having a K at the twelfth position of its MAP2 signature, instead of D, N, or S.

The term "peptidase_M24 domain", as used herein, refers to a peptidase domain, which occurs in MAP proteins. The peptidase_M24 domain is described in the pFAM database under accession number PF00557. A consensus sequence for this domain is not given in the pFAM database, but nearly 500 proteins were categorized as having a PEPTIDASE_M24 domain. This domain may be identified by its folding and tertiary structure, rather than by its primary structure, which may be variable. Different MAP proteins therefore also exhibit substantial variation in the primary structure (amino acid sequence) of this peptidase_M24 domain (see FIGS. 3A-3C). A person skilled in the art would readily know how to determine the presence of a peptidase_M24 domain in a protein sequence. One example is to submit the protein sequence to a software program capable of determining conserved domains, for example the program MotifScan as described hereinbefore. One example of a peptidase_M24 domain is given in SEQ ID NO 7, which is the peptidase_M24 domain of AtMAP1A. Another example is given in SEQ ID NO 8, which is the peptidase_M24 domain of AtMAP2B. Preferably, the MAP protein used in the methods of the present invention has a peptidase_M24 domain, which is at least 70% identical to SEQ ID NO 7 or to SEQ ID NO 8.

Optionally, for example the case of MAP2 proteins, the MAP protein useful in the methods of the present invention has at least one lysine-rich domain. Preferably such lysine-rich domain is located between the N-terminus and the MAP signature. The term "lysine-rich region" means an amino acid region, which is enriched with lysine amino acids. Typically a lysine-rich domain is an amino acid sequence of which more than 50% of the amino acids are lysine (K). For example, in AtMAP2B, 12 out of 14 continuous residues of the lysine-rich domain are lysine, which corresponds to 85% of lysine residues. Optionally a stretch of continuous lysines may be present, for example a stretch of at least 3 lysine residues, for example of 4, 5, 6 or more lysine residues. Accordingly, substantial variation between the lysine-rich domains of different MAP proteins exists, as is illustrated in FIGS. 3A-C. The lysine-rich domain of the *Arabidopsis thaliana* MAP2B protein is represented by SEQ ID NO 9.

Based on the presence and conservation of the above-mentioned structural domains, persons skilled in the art have been able to readily recognize MAP proteins of different organism, for example from plants (see Giglione et al., (2000), EMBO J. 19: p 5916-5929).

Some of the variants as mentioned hereinabove may occur in nature. Once the sequence of a variant is known, and its corresponding coding sequence, the person skilled in the art will be able to isolate the corresponding MAP gene or variant from biological material, for example by the technique of PCR. One example of such an experiment is outlined in Example 1.

Alternatively and/or additionally, the variants as mentioned above may be manmade via techniques involving, for example, mutation (substitution, insertion or deletion) or derivation. These variants are herein referred to as "derivatives", which derivatives are also useful in the methods of the present invention. Derivatives of a protein may readily be made using peptide synthesis techniques well known in the art, such as solid phase peptide synthesis and the like, or by recombinant DNA manipulations. The manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

One example of a derivative is a substitutional variant. The term "substitutional variants" of a protein refers to those variants in which at least one residue in an amino acid sequence has been removed and a different amino acid inserted in its place. Amino acid substitutions are typically of single residues, but may be clustered depending upon functional constraints placed upon the polypeptide; insertions usually are of the order of about 1-10 amino adds, and deletions can range from about 1-20 amino acids. Preferably, amino add substitutions comprise conservative amino add substitutions.

Other derivatives are "insertional variants" in which one or more amino acids are introduced into a predetermined site in the MAP protein. Insertions may comprise amino-terminal and/or carboxy-terminal fusion as well as intra-sequence insertion of single or multiple amino acids. Generally, insertions within the amino acid sequence will are of the order of about 1 to 10 amino acids. Examples of amino- or carboxy-terminal fusions include fusion of the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

Other derivatives of a MAP protein are "deletion variants", characterised by the removal of one or more amino acids from the protein.

Another "derivative" of a MAP protein is characterised by substitutions, and/or deletions and/or additions of naturally and non-naturally occurring amino acids compared to the amino acids of a naturally-occurring MAP protein. A derivative may also comprise one or more non-amino acid substituents compared to the amino acid sequence from which it is derived. Such non-amino acid substituents include for example non-naturally occurring amino acids, a reporter molecule or other ligand, covalently or non-covalently bound to the amino acid sequence. Such as reporter molecule may be bound to facilitate the detection of the MAP protein.

Another variant of a MAP protein useful in the methods of the present invention is an active fragment of a MAP protein. "Active fragments" of a MAP protein encompass at least five contiguous amino acid residues of a MAP protein, which residues retain similar biological and/or functional activity to a naturally occurring protein or a part thereof. Suitable fragments include fragments of a MAP protein starting at the second or third or further internal methionine residues. These fragments originate from protein translation, starting at internal ATG codons. Functional fragments of a MAP protein useful in practising the methods of the present invention may have one or more of the conserved domains of a MAP proteins, whilst retaining its functionality in the methods of the present invention.

According to a preferred embodiment of the present invention, a method for modifying plant growth characteristics, comprises enhanced or increased expression of a nucleic acid encoding a MAP protein. Methods for obtaining enhanced or increased expression of genes or gene products are well documented in the art and include, for example, overexpression driven by a (strong) promoter, the use of transcription enhancers or translation enhancers. The term overexpression as used herein means any form of expression that is additional to the original wild-type expression level. Preferably the nucleic acid to be introduced into the plant and/or the nucleic acid that is to be overexpressed in the plant is in the sense direction with respect to the promoter to which it is operably linked. Preferably, in the methods of the present invention a nucleic acid encoding a MAP protein is overexpressed in a plant, such as a MAP nucleic acid of SEQ ID NO 1 or a variant thereof, such as a portion of SEQ ID NO 1 or a sequence capable of hybridising therewith. However, it should be clear that the applicability of the invention is not limited to use of the nucleic acid represented by SEQ ID NO 1 nor to the nucleic acid encoding the amino acid sequence of SEQ ID NO 2, but that other nucleic acids encoding homologues, derivatives or active fragments of SED ID NO 2 may be useful in the methods of the present invention.

Alternatively and/or additionally, increased expression of a MAP gene or increased level, and/or activity of a MAP protein in a plant cell, is achieved by mutagenesis. For example these mutations may be responsible for altered control of the MAP gene, resulting in more expression of the gene, relative to the wild-type gene. Mutations can also cause conformational changes in a protein, resulting in higher levels and/or more activity of the MAP protein. Such mutations or such mutant genes may be selected, or isolated and/or introduced into the same or different plant species in order to obtain plants having modified growth characteristics. Examples of such mutants include dominant positive mutants of a MAP gene.

Modifying gene expression (whether by a direct or indirect approach) encompasses altered transcript levels of a gene. Altered transcript levels can be sufficient to induce certain phenotypic effects, for example via the mechanism of co-suppression. Here the overall effect of overexpression of a transgene is that there is less activity in the cell of the protein encoded by a native gene having homology to the introduced transgene. Therefore, according to another embodiment of the present invention, there is provided a method for modifying plant growth characteristics, comprising inhibiting or decreasing expression of a gene encoding a MAP protein or decreasing level and/or activity of a MAP protein. Examples of decreasing expression, level and/or activity of a protein are also well documented in the art and include, for example, downregulation of expression by anti-sense techniques, RNAi techniques, small interference RNAs (siRNAs) and microRNA (mRNA).

Another method for downregulation of gene expression or gene silencing comprises use of ribozymes, for example as described in Atkins et al. 1994 (WO 94/00012), Lenee et al. 1995 (WO 95/03404), Lutziger et al. 2000 (WO 00/00619), Prinsen et al. 1997 (WO 97/3865) and Scott et al. 1997 (WO 97/38116).

Gene silencing may also be achieved by insertion mutagenesis (for example, T-DNA insertion or transposon insertion) or by gene silencing strategies as described by, among others, Angell and Baulcombe 1998 (WO 98/36083), Lowe et al. 1989 (WO 98/53083), Lederer et al. 1999 (WO 99/15682) or Wang et al. 1999 (WO 99/53050).

Expression of an endogenous MAP gene may also be reduced by mutation. Such a mutation or such a mutant gene may be isolated and introduced into the same or different plant species in order to obtain plants having modified growth characteristics. Examples of such mutants include dominant negative mutants of a MAP gene.

Genetic constructs aimed at silencing gene expression may comprise the nucleotide sequence encoding a MAP protein, for example a nucleic acid represented by SEQ ID NO 1 (or a variant thereof), in a sense and/or anti-sense orientation relative to the promoter sequence. The sense and/or anti-sense copies of at least part of the endogenous gene in the form of direct or inverted repeats or in the form of a hairpin may be utilised in the methods according to the invention. The growth of plants may also be modified by introducing into a plant at least part of an anti-sense version of a nucleotide sequence encoding a MAP protein.

According to a further aspect of the present invention, there is provided genetic constructs and vectors to facilitate introduction into a plant cell and/or facilitate expression and/or facilitate maintenance of the nucleotide sequence capable of modifying expression of a nucleic acid encoding a MAP protein and/or capable of modifying level and/or activity of a MAP protein. Therefore, according to a further aspect of the present invention, there is provided a genetic construct comprising:

(a) A nucleic acid encoding a plant MAP protein or a variant thereof or a variant of a nucleic acid encoding a plant MAP protein;

(b) One or more control sequences capable of driving expression of the nucleic acid of in a plant (a); and optionally (c) A transcription termination sequence.

Constructs useful in the methods according to the present invention may be constructed using recombinant DNA technology well known to persons skilled in the art. The genetic constructs may be inserted into vectors, which may be commercially available, suitable for transformation into plants and suitable for maintenance and expression of a MAP gene in the transformed cells. Preferably the genetic construct is a plant expression vector.

The nucleic acid according to (a) is advantageously any of the nucleic acids described hereinbefore. A preferred nucleic acid is a nucleic acid represented by SEQ ID NO 1 or 3, or a variant thereof as hereinbefore defined, or is a nucleic acid encoding a protein represented by SEQ ID NO 2 or 4, or a variant thereof as hereinbefore defined.

The terms "regulatory element" and "control sequence", are used herein interchangeably and are taken in a broad context refer to regulatory nucleic acid sequences capable of driving and/or regulating expression of the sequences to which they are ligated and/or operably linked. Preferably, the control sequence of (b) is operable in a plant, most preferably the control sequence is a derived from a plant sequence. Encompassed by the terms "control sequence" are promoters. A "promoter" encompasses transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers), which alter gene expression in response to developmental and/or external stimuli, or in a tissue-specific manner. Also included within the term is a transcriptional regulatory sequence of a classical prokaryotic gene, in which case it may include a -35 box sequence and/or -10 box transcriptional regulatory sequences. The term "regulatory element" also encompasses a synthetic fusion molecule or derivative, which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest. Preferably, the promoter is operably linked to the gene of interest in a sense orientation.

Advantageously, any type of promoter may be used in the methods of the present invention. For example, a meristem-specific promoter, such as the RNR (ribonucleotide reductase), cdc2a promoter and the cyc07 promoter; or a seed-specific promoter, such as 2S2 albumin, prolamin, or oleosin promoter. A promoter may be selected in order to increase expression of a MAP protein at the moment of germination. Alternatively, a promoter expressed only in one or more of the seed tissues, such as the aleurone, embryo, scutellum or endosperm may be used. A flower-specific promoter, such as the leafy promoter, may be used if the desired outcome would be to modify expression of a MAP gene in flower organs. An anther-specific promoter may be used to modify MAP expression in male reproductive organs. Further, a root-specific promoter may be used, particularly in crops of which the roots are to be harvested; such crops include sugar beet, turnip, carrot, and potato. A vascular-specific promoter may be used or a nodule-specific promoter or a stress-inducible promoter. A cell wall-specific promoter may be used or promoters expressed preferably in one or more of the above-ground tissues of the plant, such as green tissues, shoot, stem, leaves, fruits, and young expanding issues.

According to a preferred embodiment of the invention, the MAP nucleic acid in the genetic construct as described above, is operably linked to a constitutive promoter. The term "constitutive" as defined herein refers to a promoter that is expressed substantially continuously in and substantially in all tissues of a plant. Examples of useful constitutive promoters are selected from the rice GOS2 promoter, maize GOS2 promoter, CaMV35S promoter, ubiquitin promoter, enolase promoter, actin-2 promoter and L-41 promoter or other promoters with similar expression patterns. Promoters with similar expression patterns may be found by coupling them to a reporter gene and checking the function of the reporter gene in different tissues of a plant. One suitable reporter gene is beta-glucuronidase and the calorimetric GUS staining to visualize the beta-glucuronidase activity in a plant tissue is well known to a person skilled in the art.

Optionally, one or more transcription termination sequences may also be incorporated in the genetic construct. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the genetic construct. Those skilled in the art will be aware of terminator and enhancer sequences, which may be suitable for use in the invention. Such sequences would be known or may readily be obtained by a person skilled in the art.

The genetic constructs of the invention may further include an origin of replication which is required for maintenance and/or replication in a specific cell type. One example is when a genetic construct is required to be maintained in a bacterial cell as an episomal genetic element (e.g. plasmid or cosmid molecule) in a cell. Preferred origins of replication include, but are not limited to, f1-ori and colE1 ori.

The genetic construct may optionally comprise a selectable marker gene. As used herein, the term "selectable marker gene" includes any gene, which confers a phenotype on a cell in which it is expressed to facilitate the identification and/or selection of cells, which are transfected or transformed, with a genetic construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example beta-glucuronidase, GUS), luminescence (such as luciferase) or fluorescence (Green Fluorescent Protein, GFP, and derivatives thereof). Further examples of suitable selectable marker genes include the ampicillin resistance gene (Ampr), tetracycline resistance gene (Tcr), bacterial kanamycin resistance gene (Kanr), phosphinothricin resistance gene, and the chloramphenicol acetyltransferase (CAT) gene, amongst others According to another aspect of the present invention, there is provided a method for the production of plants, having modified growth characteristics relative to corresponding wild type plants, comprising modifying expression of a nucleic acid encoding a MAP protein and/or modifying level and/or activity of a MAP protein in the plant. According to one embodiment of the invention, such a method comprises introducing into a plant cell a nucleic acid capable of modifying expression of a nucleic acid encoding a MAP protein and/or capable of modifying level and/or activity of a MAP protein.

According to a further embodiment of the invention, there is provided a method for the production of plants having modified growth characteristics, which method comprises:
(a) Introducing into a plant cell a nucleic acid encoding a MAP protein or variant thereof, or introducing a variant of a nucleic acid encoding a MAP protein; and
(b) Cultivating said plant cell under conditions promoting plant growth.

According to a further preferred embodiment, the nucleic acid of (a) is as represented by SEQ ID NO 1 or 2, or a variant thereof, or the nucleic acid of (a) encodes a MAP protein as represented by SEQ ID NO 2 or 4, or a variant thereof.

Cultivating the plant cell under conditions promoting plant growth, may or may not include regeneration of the plant cell into a plant. Cultivating the plant cell under conditions promoting plant growth may or may not include growth to reach maturity, including for example fruit production, seed formation, seed ripening and seed setting.

Methods for modifying expression of a MAP nucleic acid and/or for modifying level and/or activity of a MAP protein in a plant cell, include the introduction of the protein directly into said cell, for example by microinjection or ballistic means. Alternatively, these methods include the introduction of a nucleic acid encoding a MAP protein into a plant cell transient.

The MAP nucleic acid is preferably introduced into a plant by transformation. The term "transformation" as referred to herein encompasses the transfer of an exogenous polynucleotide into a host cell, irrespective of the method used for transfer.

Plant tissue capable of subsequent clonal propagation, whether by organogenesis or embryogenesis, may be transformed with a genetic construct of the present invention. The choice of tissue depends on the particular plant species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The nucleic acid may be transiently or stably introduced into a plant cell and may be maintained non-integrated, for example, as a plasmid. Preferably, the nucleic acid encoding a MAP protein is stably introduced into the genome of the transformed plant cell. Stable introduction into the genome of a plant cell may be achieved, for example, by using a plant transformation vector or a plant expression vector having T-DNA borders which flank the nucleic acid to be introduced into the genome.

Transformation of a plant species is now a fairly routine technique. Advantageously, any of several transformation methods may be used to introduce a MAP nucleic acid into a plant cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred transformation method for the production of transgenic plants according to the present invention, is an *Agrobacterium*-mediated transformation method.

Transgenic rice plants are preferably produced via *Agrobacterium*-mediated transformation using any of the well-known methods for rice transformation, such as the ones described in any of the following: published European patent application EP 1198985 A1, Aldemita and Hodges (Planta, 199, 612-617, 1998); Chan et al. (Plant Mol. Biol. 22 (3) 491-506, 1993); Hiei et al. (Plant J. 6 (2) 271-282, 1994); which disclosures are incorporated by reference herein as if fully set forth. In the case of corn transformation, the preferred method is as described in either Ishida et al. (Nat. Biotechnol. 1996 June; 14(6): 745-0) or Frame et al. (Plant Physiol. 2002 May; 129(1): 13-22), which disclosures are incorporated by reference herein as if fully set forth.

Generally after transformation, plant cells or cell groupings are selected for the presence of one or more of the above-mentioned selectable marker genes, which are co-transformed with the MAP gene.

The resulting transformed plant cells, cell groupings, or plant tissue may than be used to regenerate a whole plant via techniques well known to persons skilled in the art.

Subsequently, putatively transformed plant cells or plants may be evaluated, for instance using Southern analysis, for the presence of the gene of interest, copy number and/or genomic organisation. Alternatively or additionally, expression levels of the introduced nucleic acid may be undertaken using northern and/or Western analysis, both techniques being well known to persons skilled in the art.

The regenerated transformed plants may be propagated by a variety of means, such as by clonal propagation or classical breeding techniques. For example, a first generation transformed plant (T1 plant) may be selfed to give homozygous second generation transformed plants (T2 plants), which T2 plants may be further propagated through classical breeding techniques.

The generated transformed plants may take a variety of forms. For example, they may be chimeras of transformed cells and non-transformed cells; clonal transformants (e.g., all cells transformed to contain the genetic construct according to the invention); grafts of transformed and untransformed tissues (e.g., a transformed rootstock grafted to an untransformed scion).

The present invention clearly extends to plants obtainable by any of the methods according to the present invention, which plants have modified growth characteristics. The present invention dearly extends to any plant part and propagules of such plants. The present invention extends further to encompass the progeny of a primary transformed cell, tissue, organ or whole plant that has been produced by any of the aforementioned methods, the only requirement being that progeny exhibit the same genotypic and/or phenotypic characteristic(s) as the parent produced by the methods according to the invention. The invention also includes host cells having modified expression of a MAP gene and/or modified level and/or activity of a MAP protein. Particularly, the invention includes host cells comprising an isolated nucleic acid encoding a MAP protein. Such host cells preferably comprise a genetic construct as mentioned hereinabove. Preferred host cells according to the invention may be selected from bacteria, algae, fungi, yeast, insect plant or animal host cells. The present invention extends to a transgenic plant cell or plant having modified growth characteristics, which plant has modified expression of a MAP gene and/or modified level and/or activity of a MAP protein. Preferably said transgenic plant cell or plant comprising an isolated nucleic acid encoding a MAP protein or a variant thereof, more preferably comprises a genetic construct as mentioned hereinabove. The invention also extends to any part of the plants according to the invention, preferably a harvestable part, such as, but not limited to, a seed, leaf, fruit, flower, stem culture, stem, rhizome, root, tuber, bulb and cotton fiber.

The term "plant" or "plants" as used herein encompasses whole plants, ancestors and progeny of plants and plant parts, including seeds, shoots, stems, roots (including tubers), and plant cells, tissues and organs. The term "plant" also therefore encompasses suspension cultures, embryos, meristematic regions, callus tissue, gametophytes, sporophytes, pollen, and microspores. Plants that are particularly useful in the methods of the invention include all plants which belong to the superfamily Viddiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plunjuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblongs, Cryptomedia japonica, Cymbopogon* spp., *Cynthea dealbata, Cydonia oblonga, Dalbergia monetada, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythina* spp., *Eucalyptus* spp., *Euclea schimperi, Eulalia villosa, Fagopyrum* spp., *Feijoa sellowiana, Fragana* spp., *Flemingia* spp, *Freycinetia banksii, Geranium thunbergii, Ginkgo biloba, Glycine javanica, Glidcidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnate, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Omithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, trees and algae amongst others.

According to a preferred embodiment of the present invention, the plant is a crop plant such as soybean, sunflower, canola, alfalfa, rapeseed, cotton, tomato, potato, tobacco, squash, papaya, poplar, leguminosa, flax, lupinus and sorghum. According to another preferred embodiment of the present invention, the plant is a monocotyledonous plant, such as sugarcane, further preferably a cereal such as rice, maize (corn), wheat, barley, millet, rye and oats.

Accordingly, the present invention provides any of the methods as described hereinabove, or a transgenic plant as described hereinabove, wherein the plant is a monocot, preferably a cereal, more preferably wherein the plant is rice or wherein the plant is corn.

Advantageously, performance of the methods according to the present invention leads to plants having various modified growth characteristics. The term "modified" as used herein means increased or improved, decreased or changed over time and/or place. Preferably, with the methods of the present invention the plant growth characteristics are improved. The term "growth characteristic" as used herein, preferably refers to, but is not limited to yield/biomass and plant height or any one or more of the growth characteristics as described hereinbelow.

The term "yield" refers to the amount of harvestable material and is normally defined as the measurable produce of economical value of a crop. For crop plants, "yield" also means the amount of harvested material per acre or unit of production. Yield may be defined in terms of quantity or quality. The harvested material may vary from crop to crop, for example, it may be seeds (e.g. for rice, sorghum or corn when grown for seed); aboveground biomass (e.g. for corn, when used as silage), roots (e.g. for sugar beet, turnip, potato), fruits (e.g. for tomato, papaya), cotton fibers, or any other part of the plant which is of economic value. "Yield" also encompasses yield stability of the plants. High yield stability means that year after year similar yield from the progeny of the plants is obtained. "Yield" also encompasses yield potential, which is the maximum obtainable yield.

Yield may be dependent on a number of yield components, which may be monitored by certain parameters. These parameters are well known to persons skilled in the art and vary from crop to crop. For example, breeders are well aware of the specific yield components and the corresponding parameters for the crop they are aiming to improve. For example key yield parameters for corn include number of plants per hectare or acre, number of ears per plant, number of rows (of seeds) per ear, number of kernels per row, and thousand kernel weight. For silage corn, typical parameters are the above-ground biomass and energy content. Key yield parameters for rice include number of plants per hectare or acre, number of panicles per plant, number of flowers (spikelets) per panicle, seed filling rate (number of filed seeds per spikelet) and thousand kernel weight. Preferentially methods for increasing yield of rice encompass increasing number of filled seeds.

According to one particular embodiment, the term "yield" encompasses "seed yield". The plants of the present invention are characterized by increased harvested seed yield. The plants are characterized by an increased number of filled seeds and increased total weight of harvested seeds. Plants according to the present invention may also have increased total number of seeds per plant. The methods of the present invention are particularly favorable in cereals, such as rice and corn. Accordingly, a particular embodiment of the present invention relates to a method to increase yield of corn, for example seed yield, comprising modifying expression of a nucleic acid encoding a MAP protein.

The term "yield" also encompasses harvest index, which is the ratio between the harvested biomass over the total amount of biomass. The plants of the present invention are characterized by increased harvest index. Advantageously, the methods of the present invention may be used to increase harvest index of cereals and in particular the harvest index of corn or rice.

The term "yield" may also encompass Thousand Kernel Weight (TKW), which is a parameter for the biomass of a single seed. Plants of the present invention may also exhibit increased TKW. Increased TKW is also an indication of increased seed volume and/or increased seed density. Advantageously, the methods of the present invention may be used to increase the thousand kernel weight of cereals and in particular the thousand kernel weight of corn or rice may.

The term "yield" also encompasses typical biomass components, such as above-ground biomass. General biomass parameters include above-ground area and/or above-ground dry weight. The plants of the present invention are characterized by increased above-round area. Therefore, the methods of the present invention are particularly favorable for crops grown for their green issue and/or grown for their above-ground biomass. The methods of the present invention are particularly useful for grasses, forage crops (such as forage corn, clover and medicago), trees and sugar cane.

The yield increase as obtained by the methods of the invention, may result from increase or improvement of one or more of the above mentioned yield components and/or parameters.

The term "growth characteristic" as used herein also encompasses plant height. The plants according to the present invention may also exhibit increased plant height.

The invention further relates to the use of an isolated nucleic acid encoding a MAP protein or use of an isolated MAP protein to modify plant growth characteristics. Furthermore, the invention embodies the use of a MAP gene or a MAP protein as a growth regulator, such as a herbicide or a growth stimulator. Also the present invention embodies a composition comprising a MAP nucleic acid or a MAP protein or a genetic construct as herein described above, for use as a regulator of plant growth characteristics (e.g. growth regulator such as a growth stimulator). Further, this composition comprises a suitable carrier, diluent or excipient.

Alternatively, MAP genes and MAP proteins may be considered as interesting targets for agrochemical compounds, such as a growth regulator or growth stimulator. Accordingly, the invention embodies the use of a MAP gene or a MAP protein as a target of an agrochemical compound, such as or a growth regulator.

Since the plants of the present invention have excellent growth characteristics and have high yield, they are suitable for the production of enzymes, pharmaceuticals or agrochemicals. Also, they are suitable for the production of food or feed products. The invention dearly extends to enzymes, pharmaceuticals or agrochemicals as well as food or feed products isolated or produced from these plants.

Furthermore, a nucleic acid encoding a MAP protein, a MAP protein and/or the constructs of the present invention may be used in breeding programs aiming at the development of plants with increased yield. Further more, allelic variants as defined above may also be used in particular conventional breeding programs, such as in marker-assisted breeding. Such breeding programs sometimes need the introduction of allelic variation in the plants by mutagenic treatment of a plant. One suitable mutagenic method is EMS mutagenesis.

Identification of allelic variants then takes place by, for example, PCR. This is followed by a selection step for selection of superior allelic variants of the MAP sequence, which give rise to altered growth characteristics in a plant. Selection is typically carried out by monitoring growth performance of plants containing different allelic variants of the MAP sequence, for example different allelic variants of the MAP sequence of SEQ ID NO 1. Monitoring growth performance can be done in a greenhouse and/or in the field. Subsequently, plants having modified growth characteristics are selected. Such growth characteristics may be any one or more of the growth characteristics as described hereinabove. Further optional steps include crossing the selected plants in which the superior allelic variant was identified with another plant, for example a plant with an economically valuable genotype. These crossing methods may be used, for example, to make a combination of interesting phenotypic features or traits.

According to another type of breeding program, a DNA marker is identified which may be genetically linked to the gene capable of modifying expression of a MAP gene and/or modifying level and/or activity of a MAP protein in a plant (which gene may be the gene encoding the MAP protein itself or another gene capable of modifying expression of a MAP gene or capable of modifying level and/or activity of the MAP protein). This DNA marker is then used in breeding programs to select plants having modified growth characteristics. Such growth characteristics may be any one or more of the growth characteristics as described hereinabove.

The methods according to the present invention may also be practised by introducing into a plant at least a part of a (natural or artificial) chromosome (such as a Bacterial Artificial Chromosome (BAC)), which chromosome contains at least a gene encoding a MAP protein, optionally together with one or more related gene family members. Therefore, according to a further aspect of the present invention, there is provided a method for modifying plant growth characteristics comprising introducing into a plant at least a part of a chromosome comprising at least a gene encoding a MAP protein.

The present invention will now be described with reference to the following figures in which:

FIG. 1 is a map of the plant expression vector comprising an expression cassette for a MAP gene under control of a constitutive promoter. CDS0430 is the internal code for the *Arabidopsis thaliana* cDNA encoding methionine aminopeptidase MAP2B. PRO0129 is the internal code for the rice GOS2 promoter. The MAP expression cassette also comprises the double transcription termination sequence T-zein and T-rbcS-deltaGA. This expression cassette is located within the left border (LB Ti C58) and the right border (RB Ti C58) of the nopaline Ti plasmid. Cloned within these T-borders are also a screenable marker and a selectable marker both under control of a constitutive promoter and followed by a NOS transcription termination sequence. Furthermore, this vector also contains an origin of replication (pBR322 (ori+ bom) for bacterial replication and a bacterial selectable marker (Sm/SpR) for bacterial selection.

FIGS. 2A-C lists all the sequences used in the description of the present invention FIGS. 3A-C shows a multiple alignment of animal and plant MAP proteins, with the annotation of the different domains. From the N-terminus to the C-terminus: lysine-rich domain, MAP2 signature or MAP1 signature and Peptidase_M24 domain. The peptidase domain is annotated corresponding to the peptidase domain of MAP2 proteins (see for example SEQ ID NO 8). The peptidase domain of MAP1 proteins extends further than this annotation (see for example SEQ ID NO 7).

EXAMPLES

The present invention will now be described with reference to the following examples, which are by way of illustration alone.

DNA Manipulation

Unless otherwise stated, recombinant DNA techniques are performed according to standard protocols described in Sambrook (2001) Molecular Cloning: a laboratory manual, 3rd Edition Cold Spring Harbor Laboratory Press, CSH, New York or in Volumes 1 and 2 of Ausubel et al. (1988), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Cloning of CDS0430 Encoding *Arabidopsis thaliana* MAP2B

A gene encoding a methionine aminopeptidase MAP2B was amplified by PCR from an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was about 1.5 kb, and original number of clones was about $1.59 \times 10^7$ cfu. Original titre was determined to be $9.6 \times 10^5$ cfu/ml, after first amplification of $6 \times 10^{11}$ cfu/ml. After plasmid extraction, 200 ng of template was used in a 50 µl PCR mix. The primers used for PCR amplification, prm01642 with the sequence 5' ACAAGTTTGTACAAAAAAGCAGGCT-TCA CAATGGCGAGCGAAAGTCC 3' as represented by SEQ ID NO 10 and prm01643 with the sequence 5' ACCCAGCTTTCTTGTACAAAGTGGTA GGATCTGMT-CAGTAGTCGTCTC 3' as represented by SEQ ID NO 11, include an attB site for Gateway recombination (italics). PCR was performed using Hifi Taq DNA polymerase in standard conditions. A PCR fragment of 1381 bp was amplified and purified using standard methods. The first step of the Gateway procedure, the BP reaction, was then performed, during which the PCR fragment recombines in vivo with the pDONR201 plasmid to produce the entry done p1753. Plasmid pDONR201 was purchased from Invitrogen, as part of the Gateway) technology.

Example 2

Construction of Expression Cassette CD2231 (pGOS2::AtMAP2B)

The entry clone p1753 was subsequently used in an LR Gateway recombination reaction with p0640, a Gateway destination vector suitable for rice transformation. Vector p0640 contains as functional elements within the T-DNA borders, a plant selectable marker and a Gateway cassette intended for LR in vivo recombination with the sequence of interest already cloned in the entry clone. Upstream of this Gateway cassette lies the rice GOS2 promoter (PRO0129) for constitutive expression of the gene of interest (De Pater et al., Plant J. 2(6) 837-844, 1992). After the recombination step, the resulting expression vector with the expression cassette CD2231 (FIG. 1) can be transformed into *Agrobacterium* strain LBA4404 and subsequently into *Oryza sativa* var. Nipponbare plants. Transformed rice plants were allowed to grown and were examined for various growth characteristics as described in Example 3.

Example 3

Evaluation of T0, T1 and T2 Rice Plants Transformed with pGOS2::AtMAP2B

Approximately 15 to 20 Independent T0 transformants were generated. The primary transformants were transferred from tissue culture chambers to a greenhouse for growing and harvest of T1 seed. Six events of which the T1 progeny segregated 3/1 for presence/absence of the transgene were retained. "Null plants" or "Null segregants" or "Nullizygotes" are the plants treated in the same way as a transgenic plant, but from which the transgene has segregated. Null plants can also be described as the homozygous negative transformants. For each of these events, approximately 10 T1 seedlings containing the transgene (hetero- and homo-zygotes), and approximately 10 T1 seedlings lacking the transgene (nullizygotes), were selected by PCR.

Based on the results of the T1 evaluation, three events, which showed improved growth characteristics at the T1 level, were chosen for further characterisation in the T2 and further generations. To this extent, seed batches from the positive T1 plants (both hetero- and homozygotes), were screened by monitoring marker expression. For each chosen event, the heterozygote seed batches were then selected for T2 evaluation. An equal number of positive and negative within each seed batch were transplanted for evaluation in the greenhouse (i.e., for each event 40 plants, of which 20 positives for the transgene and 20 negative for the transgene, were grown). For the three events therefore, a total amount of 120 plants was evaluated in the T2 generation.

T1 and T2 plants were transferred to a greenhouse and were evaluated for vegetative growth parameters and seed parameters, as described hereunder.

(I) Statistical Analysis of Numeric Data

A two factor ANOVA (analyses of variance) corrected for the unbalanced design was used as statistical evaluation model for the numeric values of the observed plant phenotypic characteristics. The numerical values are submitted to a t-test and an F test. The p-value is obtained by comparing the t value to the t distribution or alternatively, by comparing the F value to the F distribution. The p-value stands the probability that the null hypothesis (null hypothesis being "there is no effect of the transgene") is correct.

A t-test was performed on all the values of all plants of one event. Such a t-test was repeated for each event and for each growth characteristic. The t-test was carried out to check for an effect of the gene within one transformation event, also named herein a "line-specific effect". In the t-test, the threshold for a significant line-specific effect is set at 10% probability level. Therefore, data with a p-value of the t test under 10% indicate a "line-specific" effect, meaning that the phenotype observed in the transgenic plants of that line is caused by the presence of the gene. Within one population of transformation events, some events may be under or below his threshold. This difference may be due to the difference in position of the transgene in the genome. It is not uncommon that a gene might only have an effect in certain positions of the genome. Therefore, the above-mentioned "line-specific effect" is also referred to ad "position-dependent effect".

An F-test was carried out on all the values measured for all plants of all events. An F-test was repeated for each growth characteristic. The F-test was carried out to check for an effect of the gene over all the transformation events and to verify an overall effect of the gene, also named herein "gene effect". In the F-test, the threshold for a significant global gene effect is set at 5% probability level. Therefore, data with a p-value of the F test under 5% indicate a "gene effect", meaning that the phenotype observed is caused by more than just the presence of the gene and or the position of the transgene in the genome. A "gene effect" is an indication for the wide applicability of the gene in transgenic plants.

(II) Vegetative Growth Measurements

The selected plants were grown in a greenhouse. Each plant received a unique barcode label to link unambiguously the phenotyping data to the corresponding plant. The selected plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity (which is the stage were there is no more increase in biomass) the plants were passed weekly through a digital imaging cabinet. At each time point digital images (2048×1536 pixels, 16 million colours) were taken of each plant from at least 6 different angles. The parameters described below were derived in an automated way from the digital images using image analysis software.

(a) Aboveground Area

Plant above-ground area was determined by counting the total number of pixels from above-ground plant parts discriminated from the background. This value was averaged for the pictures taken on the same time point from the different angles and was converted to a physical surface value expressed in square mm by calibration. Experiments show that the above-ground plant area, which corresponds to the total maximum area, measured this way correlates with the biomass of plant parts above-ground.

These results of the maximum above-ground area are summarized in Table 1. On average, transgenic plants show an increase in above-ground area of 10%. In one particular line the increase in above-ground area was as high as 26%. These results indicate that the MAP gene has an effect on the above-ground biomass of MAP transgenic plants.

Table 1: Maximum above-ground area of MAP transgenic T2 plants. Each row corresponds to one event, for which the average maximum above-ground area (expressed in $mm^2$) was determined for the transgenics (TR) and the null plants (null). The difference between the transgenic plants and the null plants of each event is presented in absolute values (dif.), as well as in percentage of difference (% dif). P stands for the probability produced by the t-test for each event. The last row presents the average numbers calculated from all the events. Here the p-value is produced by the F-test.

TABLE 1

| | Maximum above-ground area | | | | |
|---|---|---|---|---|---|
| Line | TR | null | dif | % dif | p-value |
| CD2231 L1 | 67117 | 66542 | 576 | 1 | 0.9193 |
| CD2231 L2 | 51901 | 49645 | 2257 | 5 | 0.6912 |
| CD2231 L3 | 77716 | 61626 | 16090 | 26 | 0.0065 |
| Overall | 65647 | 59498 | 6149 | 10 | 0.0495 |

(III) Measurement of Seed-Related Parameters

The mature primary panicles were harvested, bagged, barcode-labelled and then dried for three days in the oven at 37°

C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance. This procedure resulted in the set of seed-related parameters described below.

(a) Total Number of Filled Seeds per Plant

The number of filled seeds was determined by counting the number of filled husks that remained after the separation step. These numbers are summarized In Table 2. On average, transgenic plants show an increase in number of filled seeds of 52%. In one particular line the increase in number of filled seeds was as high as 76%. These results indicate that the MAP gene has an effect on the number of filled seeds of MAP transgenic plants.

Table 2: Number of filled seeds of MAP transgenic 72 plants. Each row corresponds to one event, for which number of filled seeds was determined for the transgenics (TR) and the null plants (null). The difference between the transgenic plants and the null plants of each event is presented in absolute values (dif.), as well as in percentage of difference (% dif). P stands for the probability produced by the t-test for each event. The last row presents the average numbers calculated from all the events. Here the p-value is produced by the F-test.

TABLE 2

| | | Number of filled seeds | | | |
|---|---|---|---|---|---|
| Line | TR | null | dif | % dif | p-value |
| CD2231 L1 | 328.2 | 216 | 112.21 | 52 | 0.0132 |
| CD2231 L2 | 157.1 | 137.2 | 19.91 | 15 | 0.6551 |
| CD2231 L3 | 412 | 233.8 | 178.21 | 76 | 0.0001 |
| Overall | 300.5 | 198.1 | 102.36 | 52 | <0.0001 |

(b) Total Seed Yield per Plant

The total seed yield was measured as total seed weight, by weighing all filled husks harvested from a plant. The values of total seed weight are summarized in Table 3. On average, transgenic plants show an increase in total seed weight of 55%. In one particular line the increase in total seed weight and thus in seed yield was as high as 79%. These results indicate that the MAP gene has an effect on the total seed weight and seed yield of MAP transgenic plants.

Table 3: Total seed weight per plant of MAP transgenic T2 plants. Each row corresponds to one event, for which the average total seed weight (in grams) was determined for the transgenics (TR) and the null plants (null). The difference between the transgenic plants and the null plants of each event is presented in absolute values (dif.), as well as in percentage of difference (% dif). P stands for the probability produced by the f-test for each event. The last row presents the average numbers calculated for all the events. Here the p-value is produced by the F-test.

TABLE 3

| | | Total seed weight | | | |
|---|---|---|---|---|---|
| Line | TR | null | dif | % dif | p-value |
| CD2231 L1 | 9 | 5.9 | 3.08 | 52 | 0.0071 |
| CD2231 L2 | 3.7 | 3.1 | 0.63 | 20 | 0.5746 |
| CD2231 L3 | 11.1 | 6.2 | 4.9 | 79 | <0.0001 |
| Overall | 8 | 5.1 | 2.83 | 55 | <0.0001 |

(c) Harvest Index

The harvest index in the present invention is defined as the ratio between the total seed yield and the above-ground area ($mm^2$), multiplied by a factor $10^6$. The values for harvest index are summarized in Table 4. On average, transgenic plants show an increase in harvest index of 36%. In one particular line the increase in harvest index and thus the increase in yield was as high as 50%. These results indicate that the MAP gene has an effect on the harvest index and on yield of the MAP transgenic plants.

Table 4: Harvest index of MAP transgenic T2 plants. Each row corresponds to one event, for which the average harvest index was determined for the transgenics (TR) and the null plants (null). The difference between the transgenic plants and the null plants of each event is presented in absolute values (dif.), as well as in percentage of difference (% dif). P stands for the probability produced by the t-test for each event. The last row presents the average numbers calculated from all the events. Here the p-value is produced by the F-test.

TABLE 4

| | | Harvest Index | | | |
|---|---|---|---|---|---|
| Line | TR | null | dif | % dif | p-value |
| CD2231 L1 | 126.4 | 84.1 | 42.24 | 50 | 0.0002 |
| CD2231 L2 | 67.4 | 59.8 | 7.63 | 13 | 0.4843 |
| CD2231 L3 | 138.6 | 99.1 | 39.52 | 40 | 0.0007 |
| Overall | 110.5 | 80.9 | 29.53 | 36 | <0.0001 |

(d) Thousand Kernel Weight

TKW is extrapolated from the number of filled seeds counted and their total weight. Some MAP transgenic plants showed an increase in Thousand kernel weight, which is an indicator of increased seed density and/or increased seed size.

(IV) Measurement of Plant Height

Plant height was determined by the distance between the horizontal lines going through the upper pot edge and the uppermost pixel corresponding to a plant part above ground. This value was averaged for the pictures taken on the same time point from the different angles (taken as described above) and was converted, by calibration, to a physical distance expressed in mm. Experiments showed that plant height measured this way correlate with plant height measured manually with a ruler. Some MAP transgenic plants showed an increase of plant height.

Example 4

Evaluation of Transgenic Corn Plants Transformed with MAP

The methods of the invention described herein are also used in corn (*Zea mays*). To this aim, a MAP encoding gene, for example a corn MAP orthologue, is cloned under control of a promoter operable in corn, in a plant transformation vector suitable for *Agrobacterium*-mediated corn transformation. The promoter operable in corn may for example be a constitutive promoter, selected from GOS2 promoters, ubiquitine promoters, L41 promoters, actine-2 promoters and enolase promoters. Methods to use for corn transformation have been described in literature (Ishida et al., Nat Biotechnol. 1996 June; 14(6):745-50; Frame et al., Plant Physiol. 2002 May; 129(1):13-22).

Transgenic (inbred) lines made by these methods may be crossed with another non-transgenic or transgenic (inbred) line or be self/sib-pollinated. Importantly, transgenic (inbred)

lines may be used as a female or male parent inheritability and copy number of the transgene are checked by quantitative real-time PCR and Southern blot analysis and expression levels of the transgene are determined by reverse PCR and Northern analysis. Transgenic events with single copy insertions of the transgene and with varying levels of transgene expression are selected for further evaluations in subsequent generations.

Progeny seeds obtained as described hereinabove are germinated and grown in the greenhouse in conditions well adapted for corn (16:8 photoperiod, 26-28° C. daytime temperature and 20-24° C. night time temperature) as well under water-deficient, nitrogen-deficient, and excess NaCl conditions. Null segregants from the same parental line (inbred line or hybrids), as well as wild type plants of the same inbred line or hybrids are used as controls. The progeny plants are evaluated on different biomass and developmental parameters, including but not limited to plant height, stalk width, nodes below ear, nodes above ear, brace roots, number of leaves, leaf greenness, leaf angle, total above-ground area time to tassel, time to silk, time to maturity, ear height, ear number, ear length, ear weight, row number, kernel number, grain moisture. Kernel traits include but are not limited to kernel size, kernel weight stanch content, protein content, and oil content are also monitored. Corn yield is calculated according to well-known methods. Corn plants transformed with a MAP protein show improved growth characteristics. More particularly they show an improvement in any one or more of the abovementioned biomass and developmental parameters.

Transgenic events that are most significantly improved compared to corresponding control lines are selected for further field-testing and marker-assisted breeding, with the objective of transferring the field-validated transgenic traits into another germplasm. The phenotyping of maize for growth and yield-related parameters in the field is conducted using well-established protocols. The corn plants are particularly evaluated on yield components at different plant densities and under different environmental conditions. Subsequent improvements for introgressing specific loci (such as transgene containing loci) from one germplasm into another is also conducted using well-established protocols including but not limited to MAS.

Example 5

Evaluation of Transgenic Plants Transformed with *Arabidopsis thaliana* MAP1A

The methods described in Examples 1, 2, 3 and 4 are also repeated with *Arabidopsis thaliana* MAP1A. To this aim, the AtMAP1A encoding gene, represented by SEQ ID NO 3, is cloned under control of a promoter operable in rice or maize, in a plant transformation vector suitable for *Agrobacterium*-mediated transformation of rice or corn. One suitable promoter is a constitutive promoter, such as a GOS2 promoter.

In case of rice plants, the protocol for isolation of cDNA and for vector construction is followed as described in Example 1 and 2, except that the primers are specific for SEQ ID NO 3. The protocols for plant transformation, plant growth and plant evaluation are followed as described in Example 3. Rice plants transformed with AtMAP1A have modified growth characteristics and show any one or more of the modified growth characteristics as described in Example 3.

In case of corn plants, the protocols for plant transformation, plant growth, plant propagation, plant selection, and plant evaluation are followed as described in Example 4. Corn plants transformed with AtMAP1A have modified growth characteristics and show any one or more of the improved growth characteristics as described in Example 4.

The invention claimed is:

1. A method for increasing seed yield and/or aboveground biomass relative to corresponding wild type plants, comprising introducing and expressing in a plant a nucleic acid encoding a plant methionine aminopeptidase (MAP protein) comprising a MAP2 signature, a peptidase M24 domain and a lysine-rich domain and having at least 95% sequence identity with the sequence of SEQ ID NO: 2, and selecting the plant having increased seed yield and/or aboveground biomass.

2. A method for the production of a plant having increased seed yield and/or aboveground biomass relative to corresponding wild type plants, comprising:
   a) Introducing into a plant cell a nucleic acid encoding a plant MAP protein comprising a MAP2 signature, a peptidase M24 domain and a lysine-rich domain, and having at least 95% sequence identity with the sequence of SEQ ID NO:2;
   b) Cultivating said plant cell under conditions promoting plant growth; and
   c) Selecting said cultivated plants having increased seed yield and/or aboveground biomass.

3. The method according to claim 1, wherein said peptidase M24 domain is at least 70% identical to SEQ ID NO: 8.

4. The method according to claim 1, wherein said peptidase M24 domain is as represented by SEQ ID NO: 8.

5. The method according to claim 2, wherein the nucleic acid of (a) is as represented by SEQ ID NO:1, or wherein said nucleic acid of (a) encodes a MAP protein as represented by SEQ ID NO:2.

6. The method according to claim 2, wherein said nucleic acid encodes a homologue having at least sequence identity with the sequence of SEQ ID NO 2.

7. The method according to claim 1, wherein said plant has increased aboveground biomass yield.

8. The method according to claim 1, wherein said plant has increased-seed yield.

9. A transgesgenic plant having modified growth characteristics, wherein said plant expresses a transgene encoding a plant MAP protein comprising a MAP2 signature, peptidase M24 domain and a lysine-rich domain, and having at least 95% sequence of SEQ ID NO:2, said plant being monocotyledonous plant.

10. The method according to claim 2, wherein said nucleic acid encodes a homologue having at least 98% sequence identity with the sequence of SEQ ID NO 2.

11. The method according to claim 2, wherein said nucleic acid encodes a homologue having at least 99% sequence identity with the sequence of SEQ ID NO 2.

* * * * *

SEQUENCE LISTING

```
<160> NUMBER OF SEQ ID NOS: 11

<210> SEQ ID NO 1
<211> LENGTH: 1320
<212> TYPE: DNA
<213> ORGANISM: Arabidopsis thaliana

<400> SEQUENCE: 1
atggcgagcg aaagtcctga tgttgctgtt gtagctccgg tggtggagaa tggcggcgct      60
gagtcctcta atggtaaaga ggaacaattg gaatctgagc tttcgaagaa gcttgagatt     120
gcagaagatg gtcaagagga gaacgatgga gaagaaggaa gcaaagctga gacttcaacg     180
aagaagaaga agaagaaaaa taaaagcaag aagaagaagg aactccctca acagactgat     240
ccaccttcaa ttcctgtcgt tgagctcttc ccatcaggag agtttcctga aggtgaaatc     300
caagagtata aggatgataa tctttggaga acaacatctg aagagaagag agagctggag     360
cgttttgaaa agccaatata taactctgtt cgccgagctg cagaagttca tcgccaggtt     420
cgtaaatatg tcagaagcat agtgaagcct ggaatgttga tgactgatat atgtgagacc     480
ctagagaata ctgttcgtaa gttgatatca gagaatggtc ttcaagctgg tattgcattc     540
cctacaggat gctctttgaa ttgggtcgct gctcattgga caccaaactc tggagataag     600
actgtacttc agtacgacga tgttatgaaa ttggactttg gaacacatat tgatgggcat     660
attattgact gtgcatttac agttgccttc aaccctatgt tcgatcctct cttagcagcc     720
```

```
tctcgtgaag ctacgtatac cggtatcaag gaagctggga tcgatgtccg tctctgtgat    780
atcggtgctg ctattcagga ggtcatggag tcttatgagg ttgaaatcaa cggaaaggtc    840
ttccaagtta aaagtatccg aaacttgaat ggtcacagca ttggaccota tcagatacat    900 gctgggaaat ctgttcctat cgtaaaagga ggcgagcaga caaagatgga agagggcgag    960
ttttatgcca tcgaaacatt tggatcaacc gggaaggat atgtgagaga agacctagaa   1020
tgtagccatt acatgaagaa ctttgacgct ggccacgtcc ccttgaggtt gcctagagca   1080
aaacaactcc ttgcaaccat taacaagaat ttctcgactc tcgccttctg cagacgttat   1140
ttggaccgca ttggtgaaac caaatactta atggctctaa agaatctttg tgactctggc   1200
attgttcagc cgtatcctcc tctgtgtgat gtgaaaggaa gctatgtatc acagtttgaa   1260
cacaccattt tactgcgacc tacttgcaaa gaagttctct ccaagggaga cgactactga   1320
```

<210> SEQ ID NO 2
<211> LENGTH: 439
<212> TYPE: PRT
<213> ORGANISM: Arabidopsis thaliana

<400> SEQUENCE: 2

```
Met Ala Ser Glu Ser Pro Asp Val Ala Val Ala Pro Val Val Glu
1               5                  10                 15

Asn Gly Gly Ala Glu Ser Ser Asn Gly Lys Glu Glu Gln Leu Glu Ser
            20                  25                  30

Glu Leu Ser Lys Lys Leu Glu Ile Ala Glu Asp Gly Gln Glu Glu Asn
        35                  40                  45

Asp Gly Glu Glu Gly Ser Lys Ala Glu Thr Ser Thr Lys Lys Lys Lys
    50                  55                  60

Lys Lys Asn Lys Ser Lys Lys Lys Glu Leu Pro Gln Gln Thr Asp
65                  70                  75                  80

Pro Pro Ser Ile Pro Val Val Glu Leu Phe Pro Ser Gly Glu Phe Pro
                85                  90                  95

Glu Gly Glu Ile Gln Glu Tyr Lys Asp Asp Asn Leu Trp Arg Thr Thr
            100                 105                 110

Ser Glu Glu Lys Arg Glu Leu Glu Arg Phe Glu Lys Pro Ile Tyr Asn
        115                 120                 125

Ser Val Arg Arg Ala Ala Glu Val His Arg Gln Val Arg Lys Tyr Val
    130                 135                 140

Arg Ser Ile Val Lys Pro Gly Met Leu Met Thr Asp Ile Cys Glu Thr
145                 150                 155                 160

Leu Glu Asn Thr Val Arg Lys Leu Ile Ser Glu Asn Gly Leu Gln Ala
                165                 170                 175

Gly Ile Ala Phe Pro Thr Gly Cys Ser Leu Asn Trp Val Ala His
            180                 185                 190

Trp Thr Pro Asn Ser Gly Asp Lys Thr Val Leu Gln Tyr Asp Asp Val
        195                 200                 205

Met Lys Leu Asp Phe Gly Thr His Ile Asp Gly His Ile Ile Asp Cys
    210                 215                 220

Ala Phe Thr Val Ala Phe Asn Pro Met Phe Asp Pro Leu Leu Ala Ala
225                 230                 235                 240

Ser Arg Glu Ala Thr Tyr Thr Gly Ile Lys Glu Ala Gly Ile Asp Val
                245                 250                 255

Arg Leu Cys Asp Ile Gly Ala Ala Ile Gln Glu Val Met Glu Ser Tyr
            260                 265                 270

Glu Val Glu Ile Asn Gly Lys Val Phe Gln Val Lys Ser Ile Arg Asn
```

```
              275                 280                 285
Leu Asn Gly His Ser Ile Gly Pro Tyr Gln Ile His Ala Gly Lys Ser
    290                 295                 300

Val Pro Ile Val Lys Gly Gly Glu Gln Thr Lys Met Glu Glu Gly Glu
305                 310                 315                 320

Phe Tyr Ala Ile Glu Thr Phe Gly Ser Thr Gly Lys Gly Tyr Val Arg
                325                 330                 335

Glu Asp Leu Glu Cys Ser His Tyr Met Lys Asn Phe Asp Ala Gly His
                340                 345                 350

Val Pro Leu Arg Leu Pro Arg Ala Lys Gln Leu Leu Ala Thr Ile Asn
            355                 360                 365

Lys Asn Phe Ser Thr Leu Ala Phe Cys Arg Arg Tyr Leu Asp Arg Ile
    370                 375                 380

Gly Glu Thr Lys Tyr Leu Met Ala Leu Lys Asn Leu Cys Asp Ser Gly
385                 390                 395                 400

Ile Val Gln Pro Tyr Pro Pro Leu Cys Asp Val Lys Gly Ser Tyr Val
                405                 410                 415

Ser Gln Phe Glu His Thr Ile Leu Leu Arg Pro Thr Cys Lys Glu Val
            420                 425                 430

Leu Ser Lys Gly Asp Asp Tyr
        435

<210> SEQ ID NO 3
<211> LENGTH: 1419
<212> TYPE: DNA
<213> ORGANISM: Arabidopsis thaliana

<400> SEQUENCE: 3
ggcgattttg agattgttct ctgattggct taatccgaga gaatcaagga attgaatggc      60
cagtgaatca gatgcatcga gcattgctac tctttcctgt gctcgctgcg agaagcctgc     120
acatcttcag tgtccgaaat gcatagactt aaagcttcct cgtgaacaag cctctttctg     180
cactcaagaa tgtttcaagg cagcttggag ctcgcacaaa tcagtacatg tgaaagctca     240
gctgtcttca atcggtgatc agaactctga tcttatttct caaggctggc tctattgcgt     300
caagaaaggc caggctagaa cacctaagct tccacacttt gattggactg gcctctaaa     360 gcaatatccc atatctacca gcgtgttgt gcctgctgag attgagaaac ctgactgggc     420
aattgatggg actcccaaag ttgaaccgaa tagtgatcta caacatgttg ttgagataaa     480
aacgcctgaa caaatccaga gaatgcgtga acctgtaaaa attgccagag aggtcctgga     540
tgcagccgct agggtgattc accccggtgt gactactgat gagattgatc gagtagttca     600
tgaagcaact attgcagcag gaggatatcc atcgcccctc aactactatt tctttccgaa     660
atcttgctgc acatctgtta atgaagtaat ttgtcatgga attccggatg ctaggaaact     720
agaagatggt gatatagtaa atgtggatgt aacagtctgt tataaaggtt gccatggtga     780
ccttaatgag acatactttg ttggaaacgt tgacgaagca tcacgtcaac tggttaagtg     840
cacatacgag tgcctggaga aagctatagc aattgttaaa cctggagtaa gatttcgtga     900
aattggagag atagtcaacc gccatgctac aatgtctggg ttatcagtgg tgagatctta     960
ttgtggtcat ggtattggag atctcttcca ttgtgctcca acattcctc actatgcaag    1020 aaacaaagca gttggagtga tgaaagcagg tcagactttc acaatcgagc caatgatcaa    1080
cgcagggggg tggagggatc gaacatggcc tgatggatgg actgcagtta ccgcagatgg    1140
aaaacgcagc gctcagtttg agcataccct attggtaacg gagactggtg ttgaggtttt    1200
```

-continued

```
aacagcgagg cttccttcat cgcctgacgt atatccttgg cttaccaagt gattaagtgt   1260
ttggttcctt tttggttgtg attcgtaaac ttgggaataa tagtgtcatc tttttgccat   1320
tatagaccat ttgatgttgt taccttgttg tctttgttta tgtaatttta ttattactat   1380
ctgaaactga atcttaaaga cagagtcata ctgtttcaa                          1419
```

<210> SEQ ID NO 4
<211> LENGTH: 398
<212> TYPE: PRT
<213> ORGANISM: Arabidopsis thaliana

<400> SEQUENCE: 4

```
Met Ala Ser Glu Ser Asp Ala Ser Ser Ile Ala Thr Leu Ser Cys Ala
1               5                   10                  15

Arg Cys Glu Lys Pro Ala His Leu Gln Cys Pro Lys Cys Ile Asp Leu
            20                  25                  30

Lys Leu Pro Arg Glu Gln Ala Ser Phe Cys Thr Gln Glu Cys Phe Lys
        35                  40                  45

Ala Ala Trp Ser Ser His Lys Ser Val His Val Lys Ala Gln Leu Ser
    50                  55                  60

Ser Ile Gly Asp Gln Asn Ser Asp Leu Ile Ser Gln Gly Trp Leu Tyr
65                  70                  75                  80

Cys Val Lys Lys Gly Gln Ala Arg Thr Pro Lys Leu Pro His Phe Asp
                85                  90                  95

Trp Thr Gly Pro Leu Lys Gln Tyr Pro Ile Ser Thr Lys Arg Val Val
            100                 105                 110

Pro Ala Glu Ile Glu Lys Pro Asp Trp Ala Ile Asp Gly Thr Pro Lys
        115                 120                 125

Val Glu Pro Asn Ser Asp Leu Gln His Val Val Glu Ile Lys Thr Pro
    130                 135                 140

Glu Gln Ile Gln Arg Met Arg Glu Thr Cys Lys Ile Ala Arg Glu Val
145                 150                 155                 160

Leu Asp Ala Ala Ala Arg Val Ile His Pro Gly Val Thr Thr Asp Glu
                165                 170                 175

Ile Asp Arg Val Val His Glu Ala Thr Ile Ala Ala Gly Gly Tyr Pro
            180                 185                 190

Ser Pro Leu Asn Tyr Tyr Phe Phe Pro Lys Ser Cys Cys Thr Ser Val
        195                 200                 205

Asn Glu Val Ile Cys His Gly Ile Pro Asp Ala Arg Lys Leu Glu Asp
    210                 215                 220

Gly Asp Ile Val Asn Val Asp Val Thr Val Cys Tyr Lys Gly Cys His
225                 230                 235                 240

Gly Asp Leu Asn Glu Thr Tyr Phe Val Gly Asn Val Asp Glu Ala Ser
                245                 250                 255

Arg Gln Leu Val Lys Cys Thr Tyr Glu Cys Leu Glu Lys Ala Ile Ala
            260                 265                 270

Ile Val Lys Pro Gly Val Arg Phe Arg Glu Ile Gly Glu Ile Val Asn
        275                 280                 285

Arg His Ala Thr Met Ser Gly Leu Ser Val Val Arg Ser Tyr Cys Gly
    290                 295                 300

His Gly Ile Gly Asp Leu Phe His Cys Ala Pro Asn Ile Pro His Tyr
305                 310                 315                 320

Ala Arg Asn Lys Ala Val Gly Val Met Lys Ala Gly Gln Thr Phe Thr
                325                 330                 335

Ile Glu Pro Met Ile Asn Ala Gly Gly Trp Arg Asp Arg Thr Trp Pro
```

```
                    340                 345                 350
Asp Gly Trp Thr Ala Val Thr Ala Asp Gly Lys Arg Ser Ala Gln Phe
        355                 360                 365

Glu His Thr Leu Leu Val Thr Glu Thr Gly Val Glu Val Leu Thr Ala
    370                 375                 380

Arg Leu Pro Ser Ser Pro Asp Val Tyr Pro Trp Leu Thr Lys
385                 390                 395

<210> SEQ ID NO 5
<211> LENGTH: 19
<212> TYPE: PRT
<213> ORGANISM: Artificial sequence
<220> FEATURE:
<223> OTHER INFORMATION: MAP1 signature consensus sequence
<220> FEATURE:
<221> NAME/KEY: MISC_FEATURE
<222> LOCATION: (1)..(1)
<223> OTHER INFORMATION: Xaa can be Met or Phe or Tyr
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Leu or Ile or Val or Met or Cys
<220> FEATURE:
<221> NAME/KEY: MISC_FEATURE
<222> LOCATION: (7)..(7)
<223> OTHER INFORMATION: Xaa can be Gly or Ser or His
<220> FEATURE:
<221> NAME/KEY: MISC_FEATURE
<222> LOCATION: (8)..(10)
<223> OTHER INFORMATION: Xaa can be any amino acid
<220> FEATURE:
<221> NAME/KEY: MISC_FEATURE
<222> LOCATION: (12)..(15)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be Leu or Ile or Val or Met
<220> FEATURE:
<221> NAME/KEY: MISC_FEATURE
<222> LOCATION: (17)..(17)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be His or Asn
<220> FEATURE:
<221> NAME/KEY: MISC_FEATURE
<222> LOCATION: (19)..(19)
<223> OTHER INFORMATION: Xaa can be Tyr or Trp or Val or His

<400> SEQUENCE: 5

Xaa Xaa Gly His Gly Xaa Xaa Xaa Xaa Xaa His Xaa Xaa Xaa Xaa Xaa
1               5                   10                  15

Xaa Xaa Xaa

<210> SEQ ID NO 6
<211> LENGTH: 17
<212> TYPE: PRT
<213> ORGANISM: Artificial sequence
<220> FEATURE:
<223> OTHER INFORMATION: MAP2 signature consensus sequence
<220> FEATURE:
<221> NAME/KEY: MISC_FEATURE
<222> LOCATION: (1)..(1)
<223> OTHER INFORMATION: Xaa can be Asp or Ala
<220> FEATURE:
<221> NAME/KEY: MISC_FEATURE
<222> LOCATION: (2)..(2)
```

```
<223> OTHER INFORMATION: Xaa can be Leu or Ile or Val or Met or Tyr
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Leu or Ile or Val or Met
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be His or Gln
<220> FEATURE:
<221> NAME/KEY: MISC_FEATURE
<222> LOCATION: (11)..(11)
<223> OTHER INFORMATION: Xaa can be Leu or Ile or Val or Met
<220> FEATURE:
<221> NAME/KEY: MISC_FEATURE
<222> LOCATION: (12)..(12)
<223> OTHER INFORMATION: Xaa can be Asp or Asn or Ser
<220> FEATURE:
<221> NAME/KEY: MISC_FEATURE
<222> LOCATION: (14)..(16)
<223> OTHER INFORMATION: Xaa can be any amino acid
<220> FEATURE:
<221> NAME/KEY: MISC_FEATURE
<222> LOCATION: (17)..(17)
<223> OTHER INFORMATION: Xaa can be Asp or Asn

<400> SEQUENCE: 6

Xaa Xaa Xaa Lys Xaa Asp Xaa Gly Xaa Xaa Xaa Xaa Gly Xaa Xaa Xaa
1               5                   10                  15

Xaa

<210> SEQ ID NO 7
<211> LENGTH: 74
<212> TYPE: PRT
<213> ORGANISM: Arabidopsis thaliana
<220> FEATURE:
<221> NAME/KEY: MISC_FEATURE
<223> OTHER INFORMATION: peptidase_M24 domain of AtMAP1A

<400> SEQUENCE: 7

Arg Ser Tyr Cys Gly His Gly Ile Gly Asp Leu Phe His Cys Ala Pro
1               5                   10                  15

Asn Ile Pro His Tyr Ala Arg Asn Lys Ala Val Gly Val Met Lys Ala
            20                  25                  30

Gly Gln Thr Phe Thr Ile Glu Pro Met Ile Asn Ala Gly Gly Trp Arg
        35                  40                  45

Asp Arg Thr Trp Pro Asp Gly Trp Thr Ala Val Thr Ala Asp Gly Lys
    50                  55                  60

Arg Ser Ala Gln Phe Glu His Thr Leu Leu
65                  70

<210> SEQ ID NO 8
<211> LENGTH: 72
<212> TYPE: PRT
<213> ORGANISM: Arabidopsis thaliana
<220> FEATURE:
<221> NAME/KEY: MISC_FEATURE
<223> OTHER INFORMATION: peptidase_M24 domain of AtMAP2B
```

```
<400> SEQUENCE: 8

Arg Asn Leu Asn Gly His Ser Ile Gly Pro Tyr Gln Ile His Ala Gly
1               5                   10                  15

Lys Ser Val Pro Ile Val Lys Gly Gly Glu Gln Thr Lys Met Glu Glu
                20                  25                  30

Gly Glu Phe Tyr Ala Ile Glu Thr Phe Gly Ser Thr Gly Lys Gly Tyr
            35                  40                  45

Val Arg Glu Asp Leu Glu Cys Ser His Tyr Met Lys Asn Phe Asp Ala
        50                  55                  60

Gly His Val Pro Leu Arg Leu Pro
65                  70

<210> SEQ ID NO 9
<211> LENGTH: 13
<212> TYPE: PRT
<213> ORGANISM: Arabidopsis thaliana
<220> FEATURE:
<221> NAME/KEY: MISC_FEATURE
<223> OTHER INFORMATION: lysine-rich domain of AtMAP2B

<400> SEQUENCE: 9

Lys Lys Lys Lys Lys Lys Asn Lys Ser Lys Lys Lys Lys
1               5                   10

<210> SEQ ID NO 10
<211> LENGTH: 47
<212> TYPE: DNA
<213> ORGANISM: Artificial sequence
<220> FEATURE:
<223> OTHER INFORMATION: Primer prm01642

<400> SEQUENCE: 10
acaagtttgt acaaaaaagc aggcttcaca atggcgagcg aaagtcc            47

<210> SEQ ID NO 11
<211> LENGTH: 49
<212> TYPE: DNA
<213> ORGANISM: Artificial sequence
<220> FEATURE:
<223> OTHER INFORMATION: Primer prm01643

<400> SEQUENCE: 11
acccagcttt cttgtacaaa gtggtaggat ctgaatcagt agtcgtctc           49
```